United States Patent  
Bajusz et al.

(10) Patent No.: US 6,593,300 B1
(45) Date of Patent: *Jul. 15, 2003

(54) (3R)-3-AMINO-4-CARBOXYBUTYRALDEHYDE DERIVATIVES INHIBITING THE RELEASE OF INTERLEUKIN-1/BETA

(75) Inventors: Sandor Bajusz, Budapest (HU); Iren Veghelyi, Budapest (HU); Klara Nemeth, Budapest (HU); Eva Barabas, Budapest (HU); Attila Juhasz, Budapest (HU); Jozsef Lango, Budapest (HU); Emilia Lavich, Budapest (HU); Zsuzsanna Mohai, Budapest (HU); Imre Moravcsik, Budapest (HU); Zsuzsanna Taschler, Budapest (HU); Gabor Toth, Budapest (HU)

(73) Assignee: Gyogyszerkutato Intezet Kft., Budapest (HU)

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/423,006

(22) PCT Filed: Apr. 22, 1998

(86) PCT No.: PCT/HU98/00040

§ 371 (c)(1),
(2), (4) Date: Feb. 7, 2000

(87) PCT Pub. No.: WO98/49189

PCT Pub. Date: Nov. 5, 1998

(30) Foreign Application Priority Data

Apr. 28, 1997 (HU) .............................. 9700816

(51) Int. Cl.[7] .................. A61K 38/00; A61K 45/00; C07K 17/00

(52) U.S. Cl. .................. 514/18; 514/19; 530/330; 530/331; 530/351; 424/85.1; 424/85.2

(58) Field of Search .............. 514/18, 19; 530/351, 530/330, 331; 424/85.1, 85.2

(56) References Cited

U.S. PATENT DOCUMENTS 6,162,828 A 12/2000 Fukuda et al. .............. 514/564

FOREIGN PATENT DOCUMENTS

| EP | 0519748 | * 12/1992 |
| WO | WO-95/35308 | * 12/1995 |
| WO | 96/30395 A | 10/1996 |

OTHER PUBLICATIONS

Bowie et al., Science, vol. 247, pp. 1306–1310, 1990.*
Houghten et al., Vaccines 86, Cold Spring Harbor Laboratory, pp. 21–25, 1986.*
Nemeth et al., Int. J. Immunopharmacol. vol. 17, No. 12, pp. 985–993, 1995.*
Graybill et al., "Preparation and Evaluation of Peptidic Aspartyl Hemiacetals as Reversible Inhibitors of Interleukin–1Beta Converting Enzyme (ICE)," International Journal of Peptide and Protein Research, vol. 44, No. 2, Aug. 1, 1994, pp. 173–182.
Mullican et al., "The Synthesis and Evaluation of Peptidyl Aspartyl Aldehydes as Inhibitors of Ice," Bioorganic & Medicinal Chemistry Letters, vol. 4, No. 19, 1994, pp. 2359–2364.

* cited by examiner

Primary Examiner—Christopher S. F. Low
Assistant Examiner—Abdel A. Mohamed
(74) Attorney, Agent, or Firm—Keil & Weinkauf

(57) ABSTRACT

The invention relates to a new (3R)-3-amino-4-carboxybutyraldehyde derivatives of general formula(I)

$$(X)_n-Y-HN-\underset{CH_2}{\overset{H_2C-COOH}{\underset{|}{C}}}-CH_2-CHO \quad (I)$$

wherein X represents a $C_{1-4}$ alkyloxycarbonyl, an optionally substituted phenyl-($C_{1-2}$ alkyloxy)-carbonyl, a $C_{1-4}$ alkylcarbonyl or an optionally substituted phenyl-($C_{1-3}$ alkyl)-carbonyl group, n represents 1 or 0, Y represents, in the case when n=1, a tetrapeptide of general formula $Y_4$-$Y_3$-$Y_2$-$Y_1$, a tripeptide of general formula $Y_3$-$Y_2$-$Y_1$ or a dipeptide of general formula $Y_2$-$Y_1$ or an amino acid residue of general formula $Y_1$, or in the case when n=0, an α-hydroxyacyl-tripeptide of general formula $Q_4$-$Y_3$-$Y_2$-$Y_1$, an α-hydroxyacyl-dipeptide of general formula $Q_3$-$Y_2$-$Y_1$ or an α-hydroxyacyl-aminoacyl residue of general formula $Q_2$-$Y_1$; wherein $Y_1$-$Y_4$ represent a residue selected from the group of the following L- or D-amino acids: alanine, alloisoleucine, cyclohexyl-glycine, phenyl-alanine, glutamine, histidine, isoleucine, leucine, lysine, methionine, pipecolic acid, proline, tyrosine and valine; and $Q_2$–$Q_4$ represent an acyl group selected from the following α-hydroxyacids of R or S configuration: 2-cycloheptyl-2-hydroxy-acetic acid, 2-cyclohexyl-2-hydroxyacetic acid, 3-cyclohexyllactic acid, 3-phenyllactic acid, 2-hydroxy-3-methylbutyric acid, 2-hydroxy-3-methylvaleric acid, mandelic acid or lactic acid, and salts thereof formed with organic or inorganic bases, and pharmaceutical compositions containing the same. The compounds of general formula (I) of the invention are valuable inhibitors of the interleukin-1β converting enzyme.

6 Claims, No Drawings

SEQUENCE LISTING

<160> NUMBER OF SEQ ID NOS: 1

<210> SEQ ID NO 1
<211> LENGTH: 4
<212> TYPE: PRT
<213> ORGANISM: Artificial Sequence
<220> FEATURE:
<223> OTHER INFORMATION: by peptide synthesis

<400> SEQUENCE: 1

Ala Tyr Val Ala

(3R)-3-AMINO-4-CARBOXYBUTYRALDEHYDE DERIVATIVES INHIBITING THE RELEASE OF INTERLEUKIN-1/BETA

This invention relates to new (3R)-3-amino-4-carboxybutyraldehyde derivatives of general formula (I),

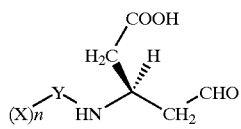

wherein
X represents a $C_{1-4}$ alkyloxycarbonyl, an optionally substituted phenyl-($C_{1-2}$ alkyloxy)carbonyl, a $C_{1-4}$ alkylcarbonyl or an optionally substituted phenyl$C_{1-3}$ alkyl)carbonyl group, n represents 1 or 0,
Y represents, in the case when n=1, a tetrapeptide of general formula $Y_4$-$Y_3$-$Y_2$-$Y_1$, a tripeptide of general formula $Y_3$-$Y_2$-$Y_1$ or a dipepbide of general formula $Y_2$-$Y_1$ or an amino acid residue of general formula $Y_1$, or in the case when n=0, an α-hydroxyacyl-tripeptide of general formula $Q_4$-$Y_3$-$Y_2$-$Y_1$, an α-hydroxyacyl-dipeptide of general formula $Q_3$-$Y_2$-$Y_1$ or an α-hydroxyacyl-aminoacyl residue of general formula $Q_2$-$Y_1$,
wherein
$Y_1$-$Y_4$ represent a residue selected from the group comprising the following L- or D-amino acids: alanine, alloisoleucine, cyclohexyl-glycine, phenylalanine, glutamine, histidine, isoleucine, leucine, lysine, methionine, pipecolic acid, proline, tyrosine and valine, and
$Q_2$-$Q_4$ represent an acyl group selected from the following α-hydroxyacids of R or S configuration: 2cloheptyl-2-hydroxyacetic acid, 2-cyclohexyl-2-hydroxyacetic acid, 3-cyclo-hexyllactic acid, 3-phenyllactic acid, 2-hydroxy-3-methylbutyric acid, 2-hydroxy-3-methyl-valeric acid, mandelicacid or lactic acid,
and salts thereof formed with organic or inorganic bases, and pharmaceutical compositions containing the same.

The compounds of general formula (I) of the invention have valuable therapeutic properties, particularly an inhibitory effect on the interleukin-1β converting enzyme. Accordingly, they may be applied for the treatment of various inflammatory diseases such as arthritis, colitis, hepatitis, glomerulonephritis and myocarditis, as well as septic shock.

Particularly valuable representatives of the compounds of general formula (I) of the invention are the following:
(3R)-3-(acetyl-L-tyrosyl-L-valyi-L-alanylamino)-4-carboxy-butyraldehyde, (3R)-3-(ethoxycarbonyl-L-alanyl-L-tyrosyl-L-valyl-L-alanyl-amino)-4-carboxybutyraidehyde, (SEQ ID NO:1)
(3R)-3-(methoxycarbonyl-L-alanyl-L-tyrosyl-L-valyl-L-alanyl-amino)-4-carboxybutyraldhyde, (SEQ ID NO:1)
(3R)-3-(acetyl-L-tyrosyl-L-valyl-L-histidylamino)-4-carboxy-butyraldehyde,
(3R)-3-(acetyl-L-tyrosyl-L-valyl-L-glutaminylamino)-4-carboxybutyraldehyde,
(3R)-3-(acetyl-L-tyrosyl-L-isoleucyl-L-alanylamino)-4-carboxybutyraldehyde,
(3R)-8-(acetyl-L-tyrosyl-L-alloisoleucyl-L-alaylamino)-4-carboxybutyraldehyde,
(3R)-3-(acetyl-L-tyrosyl-L-leucyl-L-alanylamino)-4-carboxy-butyraldehyde,
(3R)-3-(acetyl-L-tyrosyl-L-methionyl-L-alanylamino)-4-carboxybutyraldehyde,
(3R)-3-(acetyl-L-tyrosyl-L-cyclohexylglycyl-L-alanylamino)-4-carboxybutyraldehyde,
(3R)-3-(acetyl-L-phenylalanyt-L-valyl-L-alany lamino)-4-carboxybutyraldehyde,
(3R)-3[(2S)-(2-hydroxypropionyl)-L-tyrosyl-L-valyl-L-alanyl-amino]-4-carboxybutyraldehyde,
(3R)-3-[(2-hydrxypropionyl)-L-tyrosyl-L-valyl-L-pipecolinylamino]-4-carboxybutyraldehyde,
(3R)-3-[(2S)-(2-hydroxypropionyl)-L-tyrosyl-L-valyl-L-prolylamino]-4-carboxybutyraldehyde,
(3R)-3-[(2S)-(2-hydroxy-3-phenylpropionyl)-L-vayl-L-alanylamino]-4-carboxybutyraldehyde,
(3R)-3-[(2S)-(2-hydroxy-3cyclohexylpropionyl)-L-valyl-L-alanylamino]-4-carboxybutyraldehyde,
(3R)-3-[(2S)-(2-cyclohexyl-2-hydroxyacetyl)-L-alanylamino]-4-carboxybutyraldehyde,
(3R)-3-[(2S)-(2-cycloheptyl-2-hydroxyacetyl)-L-alanylamino]-4-carboxybutyraldehyde,
(3R)-3-[(2S)-(2-hydroxy-3-methylbutiryl)-L-alanylamino)]-4-carboxybutyraldehyde,
(3R)-3-[(2S,3S)-(2hydroxy-3-methylvaleryl)-L-alanylamino)]-4-carboxybutyraldehyde,
and their salts formed with organic or inorganic bases.

Particularly preferred compounds of general, formula (I) of the invention are (3R)-3-(acetyl-L-tyrosyl-L-valyl-L-alanyl-amino)-4-carboxybutyraldehyde and (3R)-3-(ethoxycarbonyl-L-alanyl-L-tyrosyl-L-valyl-L-alanylamino)-4-carboxy-butyraldehyde and their salts formed with organic or inorganic bases (SEQ ID NO:1)

Definitions

The abbreviations of the amino acids, their substituents and peptides built up therefrom are in accordance with the prior art, e. g. J. Biol. Chem. 264, 668 (1989).
Amino Acids:
Arg=L-arginine [(2R)-2-amino-5-guanidino-pentanoic acid],
Ala=L-alanine [(2S)-2-aminopropionic acid],
Ale=L-alloisoleucine [(2S,3R)-2-amino-3-methylvaleric acid],
Asn=L-asparagine [(2S)-2-amino-3-carbamoylpropionic acid],
Asp=L-aspartic acid [(2S)-2-amino-3-arboxypropionic acid],
hAsp=L-β-homoaspartic acid [(3R)-3-amino-4-carboxy-butyric acid],
Chg=L-2-cyclohexylglycine [(2S)-2-amino-2-cyclohexyl-acetic acid],
Gln=L-glutamine [(2S)-2-amino-4-carbamoylbutyric acid],
Glu L-glutamic acid [(2S)-2-amino-4-carboxybutyric acid],
Gly=glycine (2-aminoacetic acid),
His=L-histidine [(2S)-2-amino-3-(imidazolyl)propionic acid],
Ile=L-isoleucine [(2S,3S)-2-amino-3-methylvaleric acid],
Leu=L-leucine [(2S)-2-amino-4-methylvaleric acid)],
Lys=L-lysine [(2S)-2,6-diaminocaproic acid],
Met=L-methionine [(2S)-2-amino-4-methylmercapto-butyric acid], Phe=3-phenyl-L-alanine [(2S)-2-amino-3-phenylpropionic acid],
Pip=L-pipecolic acid [(2S)-piperidine-2-carboxylic acid],
Pro=L-proline [(2S)pyrrolidine-2-carboxytic acid],
Ser=L-serine [(2S)-2-amino-3-hydroxypropionic acid],
Tyr=L-tyrosine [(2S)-2-amino-3-(4-hydroxyphenyl)-propionic acid],
Val=L-valine [(2S)-2-amino-3-methylbutyric acid].
α-Hydroxyacids:
cHga=L-2-cycloheptylglycolic acid [2S)-2-cycloheptyl-2-hydroxyacetic acid],
Hma=L-hexahydromandelic acid [(2S)-2-cyclohexyl-2-hydroxyacetic acid],
Hmb=(2S)-2-hydroxy-3-methylbutyric acid,
Hmv=(2S)(3S)-2-hydroxy-3-methylvaleric acid],
Hpl=L-hexahydrophenyllactic acid [(2S)-2-hydroxy-3-cyciohexylpropionic acid],
Lac=L-lactic acid [(2S)-2-hydroxypropionic acid],
Man=L-mandelic acid [(2S)-2-phenyl-2-hydroxyacetic acid)],
Pla=L-phenyllactic acid [(2S)-2-hydroxy-3-phenylpropionic acid],
Pla(OH)=L-(4-hydroxyphenyl)lactic acid [(2S)-2-hydroxy-3-(4-hydroxyphenyl)propionic acid]
Substituens:
Ac=acetyl,
Boc=t-butoxycarbonyl,
Eoc=ethoxycarbonyl,
DCB=2,6-dichloro-benzoyloxy,
DMB=2,6-dimethyl-benzoyloxy,
Moc=methoxycarbonyl,
PhP=3-phenyl-propionyl,
Z=benzyloxycarbonyl,
Z(OH)=4-hydroxy-benzyloxycarbonyl.

Peptides and Derivatives

The abbreviations of amino acids alone represent the respective L-amino acid. The D-amino acid is marked separately, e. g. 3-phenyl-D-alanine=D-Phe. The hyphen before and after the amino acid abbreviation designates a missing hydrogen atom from the amino group or a missing hydroxy group from the carboxy group, resp. Accordingly, Eoc-Ala-Tyr-Val-Ala-hAsp-H represents ethoxycarbonyl-L-alanyl-L-tyrosyl-L-valyl-L-alanyl-3-amino-4-carboxy-butyraldehyde.

Description of the Known Art

Interleukin-1 (IL-1), a cytokine, formed e.g. in monocytes upon the action of infections, tissue injury or antigens, exerts manifold local and systemic effects [C. A. Dinarello: Blood 77, 1627 (1991)]. It is best known as an inflammation inducing cytokine but it also promotes the proliferation and differentiation of various cells while in other cells it influences the synthesis and release of enzymes, hormones, blood clotting factors and proteins of the acute phase. IL-1 is responsible for triggering inflammatory processes and maintaining inflammations followed by tissue injury [C. A. Dinarello and S. M. Wolff: N. Engl. J. Med., 328, 106 (1993)]. The direct pathologic role of IL-1 has been confirmed in rheumathoid arthritis and osteoarthritis (increased IL-1 production in the cells and high levels in the plasma and synovial fluid are indicators of these diseases). Furthermore, it is an important mediator in several other diseases such as cholangitis, encephalitis, endocarditis, pancreatitis and vasculitis. In other diseases such as disseminated intravascular coagulation, developing as a result of infections, and/or tissue injuries, it exerts its damaging action together with inflammatory cytokines (TNFα). In further diseases the immunemodulator, immunadjuvant role of IL-1 becomes predominant, e. g. in the graft versus host disease, graft rejection, acute and delayed hypersensitivity and autoimmune diseases, e. g. type I diabetes mellitus and sclerosis multiplex. As an autocrine growth factor IL-1 is playing a role in certain neoplastic diseases, primarily in acute myelogenic leukaemia, IL-1 exists in two structurally different forms, IL-1α and IL-1β, encoded by two different genes [C. J. March: Nature 315, 641 (1985)]. IL-1α and IL-1β are synthesized in the form of a precursor protein with 271 and 269 amino acid residues, resp., which are transformed by limited proteolysis into the mature protein with 158 and 153 members, resp. [B. S. Mosley et al.: J. Biol Chern. 262, 2941 (1987)]. Monocytes, macrophages, lymphocytes T and B, NK cells, astrocytes, fibroblasts, chondrocytes, endothelial cells, thymic epithelial cells and glyoma cells all are able to synthesize IL-1. The two forms of IL-1 induce basically similar effects on the same IL-1 receptor. The precursor and the mature form of IL-1a are both active while only the 153 membered mature form of IL-1β exerts biological activity [R. A. Black et al.: J. Biol Chem. 263, 9437 (1989)]. IL-1β is the agent produced in greater amounts, this is getting into the blood circulation, consequently the systemic effects of IL-1 may be attributed to IL-1β.

During the activation of the IL-1β precursor (proIL-1β) the enzyme inducing the conversion (ICE: IL-1β converting enzyme) is cleaving the bonds between Asp27 and Gly28 as well as Asp116 and Ala117. The resuit of the later cleavage is the 117–269 fragment, the mature, biologically active IL-1β[P. R. Sleath et al.: J. Biol Chem. 265, 14526 (1990) and N. A. Thornberry et al.: Nature 356, 768 (1992)]. The amino acid sequence of the cleavage sites and their proximity:

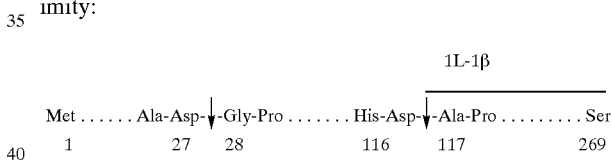

ICE is also synthesized intracellularly as a precursor peptide with 404 amino acid residues. In this molecule 4 Asp-X bonds are cleaved autocatalytically. The active enzyme is built up from the two 120–297 (p20) and 317–404 (p10) fragments which exist in the tetrameric form (p20)$_2$/(p10)$_2$ [K. P. Wilson et al.: Nature 370, 270 (1994)].

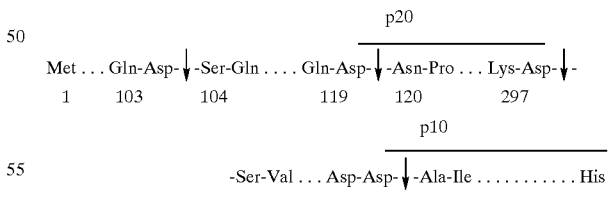

In the course of identification ICE proved to be a cysteine protease: it contained a functional cysteine moiety (Cys285) which could be easily alkylated and it was inhibited by peptide-diazomethylketone. This type of inhibitor can only react with cysteine proteases. ICE was not inhibited by the other traditional cysteine protease inhibitor, the epoxy type E64 [R. A. Black and al.: FEBS Lett 247, 389 (1989)] but was inhibited by the characteristic serine protease inhibitor 3,4-dichloro-isocoumarine [K. P. Wilson et al.: Nature 370, 270 (1994)]. The substrates are cleaved by ICE after the Asp residue which is represented in the general formula of the substrates ($P_n$- .... -$P_2$-$P_1$↓-$P_1$'- .... -$P_n$'-) by $P_1$ but the amino acid residue preceding it—$P_2$—may be quite different (Ala, His, Gln, Lys, Asp). This role of $P_1$ can be observed in serine proteases while the substrate specificity of cysteine proteases is more dependent on the type of $P_2$ (L. Polgar Mechanism of Protease Action, CRC Press, Boca Raton, 1989, Chapter 4). All these findings suggest that ICE is a specific cysteine protease with properties different from those of known cysteine proteases [M. A. Ator and R. E. Dolle: Current Pharmaceutical Design 1, 191 (1995)].

Attempts to inhibit IL-1β are justified by its pathological role. Its function may be blocked by inhibiting its biosyntheses, release or receptorinding. From the manifold strategies the search for receptor antagonists has found greatest attention. Unfortunately, the low molecular weight agents most useful in therapy proved to be poor antagonists. The glucocorticoids, the best inhibitors of biosynthesis, had different main activity and, in addition, had severe side effects, too. The strategies for inhibiting IL-1 became broader with the discovery of ICE, the proIL-1β converting enzyme. By recognising the structure and function of ICE, low molecular weight inhibitors may be developed, which inhibit the autocatalysis of the enzyme, the development of active ICE and/or its proteolytic action an proIL-1β whereby no active IL-1β is released, consequently no IL1β appears in the blood circulation.

It is known that both cysteine and serine proteases may be inhibited by peptide aldehydes with an amino acid sequence which is similar to the sequence prior to the peptide bond (↓) cleaved in the substrates: $P_n$- .... -$P_2$-$P_1$ [J. C. Powers and J. W. Harper: in *Protease Inhibitors* (A. J. Barrett and G. Salvesen, eds.), Elsevier, Amsterdam, 1986, Chapter 3; D. H. Rich: idem, Chapter 4]. The peptide $P_1$ and serine protease $S_1$ subunits, and the peptide $P_2$ and cysteine protease $S_2$ subunits are participating in the recognition of the respective sites. First these are coupled to one another, this is rapidly followed by the interaction of further $P_n/S_n$ subunits, then the addition between the α—CHO group of the $P_1$ amino acid and the active OH group of the serine or the SH group of the cysteine in the proteases. A hemiacetal and a thiohemiacetal are formed, resp., which are non-productive analogues of the tetrahedral intermediate formed with the CO—NH group of the substrate to be cleaved. The reaction is reversible, the peptide aldehydes are reversible inhibitors of the serine and cysteine proteases.

Analogue peptide diazomethyl-ketones or halomethyl- and acyloxy-methyl-ketones are suitable irreversible inhibitors of cysteine proteases. The C-terminal group of the $P_1$ amino acid residue in these inhibitors is α—CO—$CHN_2$ and α—CO—$CH_2$—X (X=halogen or acyloxy group), resp. In the first phase of their reaction with cysteine proteases a thiohemiacetal is formed—similarly to the above reaction—, which is converted later into the more stable S-alkyl form—α—CO—$CH_2$— —, i e. the $P_n$- .... -$P_2$-$P_1$ peptide moiety of the inhibitor is bound to the cysteine S atom of the protease by a methylene bridge.

In the following the proximity of the cleavage sites in proIL-1β—the 23–32 (A) and 112–121 (B) sequence—is represented as a substrate fragment, wherein each 5 amino acid moiety preceding and following the cleavage site (↓) is indicated by $P_5$-$P_1$ and $P_1$'-$P_5$', resp.:

$P_5$ $P_4$ $P_3$ $P_2$ $P_1P_1$' $P_2$' $P_3$' $P_4$' $P_5$'

A: Phe-Phe-Glu-Ala-Asp↓Ala-Pro-Lys-Gln-Met
B: Ala-Tyr-Val-His-Asp↓Ala-Pro-Val-Arg-Ser

The first reversible and irreversible inhibitors of ICE, the Ac-Tyr-Val-Ala-Asp-H tetrapeptide aldehyde and the analogue Ac-Tyr-Val-Ala-Asp-$CHN_2$ diazomethylketone, resp., were described by N. A. Thornberry et al. [Nature 356, 768 (1992) and K. T. Chapman et al.: published European patent application No. 519,748]. It is apparent that in agreement with the above sequence of the peptide derivatives is derived from the substrate fragments: $P_4$ and $P_3$ from B, $P_2$ from A and $P_1$ from both. In the aldehyde series the tripeptide (Z-Val-His-Asp-H) and pentapeptide (Eoc-Ala-Tyr-Val-His-Asp-H) corresponding to sequence B were prepared (together with the analogue Eoc-Ala-Tyr-Val-Ala-Asp-H containing Ala at position $P_2$) [I. Faust et al.: in Peptides, Proceedings of the 13th American Peptide Symposium, 1993 (R. S. Hodges and J. A. Smith, eds.) ESCOM, Leyden, 1994, pp. 589–591]. Within the scope of irreversible inhibitors after the above diazomethylketone mostly acyloxymethylketones, e. g. Ac-Tyr-Val-Ala-Asp$CH_2$DMB and PhP-Val-Ala-Asp$CH_2$DMB [N. A. Thornberry et al.: Biochemistry 33, 3934 (1994)], and Z-Val-Ala-Asp$CH_2$DCB [C. V. C. Prasad et al.: Bioorg. Med. Chem. Lett 5, 315 (1995) and R. E. Dolle et al.: published European patent applications Nos. 623,592 and 623,606] were prepared. Furthermore, derivatives were synthesized wherein the aspartyl-methyloxyacyl or aspartyl-methyloxyhetero)aryl groups were coupled to other peptide residues or other non-peptide moieties [e. g. R. E. Dolle et al.: published international patent application WO 95 25,741 (1995) and published European patent application No. 644, 198)].

The international publication WO 95/35308A describes compounds having a structure which is near to the structure of the compounds according to the invention. Although this reference claims compounds/peptides comprising β-amino-aldehyde structure on the terminal C, which is similar to that of the compounds according to the invention, the examples of this reference illustrate exclusively compounds/peptides comprising α-amino-aldehyde (ketone) structural units on the terminal C.

In in vitro cellular models IL-1β release is inhibited by both reversible and irreversible ICE inhibitors at values of $IC_{50} \leq 10 \mu M$ [D. K. Miller et al.: Ann. N. Y. Acad. Sci. 696, 133 (1994); P. R. Eiford et al.: Br. J. Pharmacol. 115, 601 (1995); K. Németh et al.: Int. J. Immunopharmac. 17, 985 (1995)]. The in vivo efficacy of ICE inhibitors was also confirmed in the case of Ac-Tyr-Val-Ala-Asp-H and Z-Val-Ala-Asp-$CH_2$DCB in the mouse, in the "tissue chamber" model as well as in lipopolysaccharide (LPS) induced fever or septic shock models [B. E. Miller et al.: J. Immunol: 154, 1331 (1994); D. S. Fletcher et al.: J. Interf. Cytok. Res 15, 243 (1995); P. R. Elford et al.: Br. J. Pharmacol. 115, 601 (1995)].

Short Description of the Invention

It is the objective of the present invention to prepare active inhibitors of interleukin-1β release.

It was unexpectedly found that the release of interleukin-1β from blood cells can be inhibited with the peptidyl derivatives of (3R)-3-amino-4-arboxybutyraldehyde of the invention, i. e. with peptide aldehydes wherein the $P_1$ subunit is a β-aminoaldehyde. The (3R)-3-amino-4-carboxybutyraldehyde is a homologue of the known L-aspartic acid α-aldehyde [(2R)-2-amino-3arboxy-propionaldehyde)], i. e. L-β-homo-aspartic acid α-aldehyde (hAsp-H). The inhibiting effect of β-aminoaldehydes, or their acyl or peptidyl derivatives, resp., on cysteine or serine proteases is not known yet in the literature. C. V. C. Prasad et al. [Bioorg. Med. Chem. Lett. 5, 315 (1995)] have proved that the α—CO group of the Asp residue, the $P_1$ amino acid moiety of the inhibitor, is playing a major role in enzyme inhibition. Namely, while Z-Asp-$CH_2$DCB [i. e. Z-NH—CH($CH_2$COOH)—CO—$CH_2$DCB] has significant ICE inhibiting effect, Z-AhAsp-$CH_2$DCB [i. e. Z-NH—CH($CH_2$COOH)—$CH_2$—CO—$CH_2$DCB] containing a β—CO group is ineffective.

Detailed Description of the Invention

This invention relates to new (3R)-3-amino-4-carboxybutyraldehyde derivatives of general formula (I), wherein X represents a $C_{1-4}$ alkyloxycarbonyl, an optionally substituted phenyl-($C_{1-2}$' alkyloxy)carbonyl, a $C_{1-4}$ alkylcarbonyl or an optionally substituted phenyl-($C_{1-3}$ alkyl)-carbonyl group, n represents 1 or 0, Y represents, in the case when n=1, a tetrapeptide of general formula $Y_4$-$Y_3$-$Y_2$-$Y_1$, a tripeptide of general formula $Y_3$-$Y_2$-$Y_1$ or a dipeptide of general formula $Y_2$-$Y_1$ or an amino acid residue of general formula $Y_1$, or in the case when n=0, an α-hydroxyacyl-tripeptide of general formula $Q_4$-$Y_3$-$Y_2$-$Y_1$, an α-hydroxyacyl-dipeptide of general formula $Q_3$-$Y_2$-$Y_1$ or an α-hydroxyacyl-aminoacyl residue of general formula $Q_2$-$Y_1$, wherein $Y_1$-$Y_4$ represent a residue selected from the group of the following L- or D-amino acids: alanine, alloisoleucine, cyclohexyl-glycine, phenylalanine, glutamine, histidine, isoleucine, leucine, lysine, methionine, pipecolic acid, proline, tyrosine and valine, and $Q_2$-$Q_4$ represent an acyl group selected from the following α-hydroxyacids of R or S configuration: 2-cycloheptyl-2-hydroxyacetic acid, 2-cyclohexyl-2-hydroxyacetic acid, 3-cyclohexyllactic acid, 3-phenyllactic acid, 2-hydroxy-3-methylbutyric acid, 2-hydroxy-3-methyl-valeric acid, mandelic acid or lactic acid, and salts thereof formed with organic or inorganic bases, and pharmaceutical compositions containing the same.

Compounds of the instant invention are conveniently prepared using the procedures described generally below and more explicitly described in the Examples hereinafter.

The compounds of general formula (I), wherein X, n and Y have the same meaning as above, are prepared by coupling a (3R)-3-amino-4-carboxybutyraldehyde derivative provided with suitable protecting groups, e. g. (3R)-3-amino-4-t-butoxycarbonyl-butyraidehyde diethyl acetal, with the $(X)_n$-Y peptide residue, removing the protecting groups from the product and isolating the peptide derivative of general formula (I) in the form of an organic or inorganic salt.

(3R)-3-Amino-4-t-butoxycarbonyl-butyraidehyde diethyl acetal, a protected derivative of a (3R)-3-amino-4-carboxybutyraldehyde, a suitable key intermediate in the synthesis of compounds of general formula (I), is prepared by refluxing benzyloxycarbonyl-4-t-butyl-L-aspartyldiazomethane in methanol solution in the presence of $Ag_2O$, converting the thus-formed (3R)-3-(benzyloxycarbonylamino)-4-t-butoxybutyric acid methyl ester after saponification to the 3,5-dimethyl-pyrazolide, then reducing the latter compound by lithium-aluminium hydride, transforming the aldehyde produced with orthoformic acid ester into diethyl acetal, cleaving the benzyloxycarbonyl group by hydrogenation and isolating the obtained (3R)-3-amino-4-t-butoxycarbonyl-butyraldehyde diethyl acetal.

The peptide moiety of general formula $(X)_n$-Y of the compounds of general formula (I) is prepared in the case of n=1 by starting at the C-terminal amino acid ester of general formula $Y_1$ according to the usual methods used in peptide synthesis, and building up the desired tetrapeptide moiety of general formula $Y_4$-$Y_3$-$Y_2$-$Y_1$ tripeptide moiety of general formula $Y_3$-$Y_2$-$Y_1$ or dipeptide moiety of general formula $Y_2$-$Y_1$ and coupling to these or, if desired, to the $Y_1$ ester, the acyl group of general fonrula X, saponifying the obtained acyl-peptide ester or acyl-amino acid ester and isolating the produced acyl peptide or acyl-amino acid.

The peptide moiety of general formula $(X)_n$-Y of the compounds of general formula (I) is prepared in the case of n=0 when α-hydroxy-acylamino acid moieties are used as building blocks, e. g. the α-hydroxy-acyl-tripeptide moiety of general formula $Q_4$-$Y_3$-$Y_2$-$Y_1$ α-hydroxy-acyl-dipeptide moiety of general formula $Q_3$-$Y_2$$Y_1$ or α-hydroxy-acyl-aminoacyl moiety of general formula $Q_2$-$Y_1$, by acylating the tripeptide moiety of general formula $Y_3$-$Y_2$-$Y_1$, the dipeptide moiety of general formula $Y_2$-$Y_1$ or amino acid moiety of general formula $Y_1$ in ester form with an α-hydroxy-acid of general formula $Q_4$ or $Q_3$ or $Q_2$, protected at the α-hydroxy group, e. g. with a tetrahydropyranyl group, saponifying the produced α-hydroxy-acyl-peptide ester or α-hydroxy-acyl-arnino acid ester and isolating the α-hydroxy-acyl-tripeptide of general formula $Q_4$-$Y_3$-$Y_2$-$Y_1$ α-hydroxy-acyl-dipeptide of general formula $Q_3$-$Y_2$-$Y_1$ or α-hydroxy-acylamino-acid of general formula $Q_2$-$Y_1$.

The compounds of general formula (I) of the invention, wherein X, n and Y have the same meaning as above, inhibit the release of IL-1β from e. g. human blood monocytes. An in vitro method was used for measuring, this effect of the compounds. Principle of the method: upon the action of a lipopolysaccharide (LPS), a constituent of the cell wall of Gram negative bacteria, serving as antigen, immunecells are activated in the blood and produce characteristic factors (e. g./cytokines and enzymes) and then release them partially in the environment. For the production of inflammatory cytokines (e. g. IL-1) appearing during cell activation monocytes represent the most important cellular elements in the blood. On the basis of investigations of DeForge [J. Immunol. 148, 2133 (1992)] and DeGroote [Cytokine. 4, 239 (1992)] the monocytes were not separated from the blood but heparinized whole human blood was used for the assay. The blood was incubated with the peptide aldehydes and the inducing LPS in a $CO_2$ thernostate for 24 hours at 37° C. After inducing the blood with LPS the amount of IL1β was measured in the blood plasma by EILISA (Enzyme Linked Immunosorbent Assay) method. The values measured in the treated groups (LPS plus peptide aldehyde) were related to the values measured in the control group (treated only with LPS). The inhibitory effect of peptide aldehydes on IL1β production was characterized by IC50 values. The $IC_{50}$ values were calculated from the data of peptide aldehydes measured at 5 different concentrations. According to these data the IL-1β release from human whol blood was inhibited by Ac-Tyr-Val-Ala-hAsp-H, Eoc-Ala-Tyr-Val-Ala-hAspH (SEQ ID NO:1) and Lac-Tyr-Val-Ala-hAsp-h at $IC_{50}$ values of 1.82±0.79, 7.09±0.10 and 11.0±3.5, resp.

The compounds of the invention and their pharmaceutically acceptable salts are used for therapeutic purposes alone or preferably in the form of pharmaceutical formulations. The invention also refers to these formulations.

The pharmaceutical formulations comprise an effective amount of a compound of general formula (I) or a pharmaceutically acceptable salt thereof and known pharmaceutically acceptable carriers, filling materials, diluents and/or other pharmaceutical excipients.

The above carriers, diluents or filling materials can be water, alcohols, gelatine, lactose, saccharose, starch, pectin, magnesium stearate, stearic acid, talcum, various oils of animal or plant origin, furthermore glycols, e. g. propyleneglycol or polyethylene glycol. The pharmaceutical excipients can be preservatives, various natural or synthetic emulgeators, dispersing or wetting agents, colouring materials, flavouring agents, buffering materials, materials promoting disintegration and other materials improving the bioavailability of the active ingredient.

The pharmaceutical compositions of the invention can be prepared in usual formulations, such as oral compositions (administered through the mouth, such as tablets, capsules, powders, pills, dragees or granulates) as well as parenteral compositions (drugs administered by avoiding the gastrointestinal system, such as injections, infusions, suppositories, plasters or ointments).

The therapeutic dose level of the compounds of the invention depends on the individual health status and age of the patients and may vary accordingly; consequently, its level is fixed by the physician designing treatment. The daily oral or parenteral (e. g. i. v.) dose may be 0.01 to 1000 mg/kg body weight, preferably 0.25 to 20 mg/kg body weight.

This invention also relates to a method of treatment for patients (including man and/or mammalian animals) suffering from disorders or diseases which can be attributed to IL-1β/ICE as previously described, and more specifically, a method of treatment involving the administration of IL-1β/ICE inhibitors of formula (I) as the active constituents.

Accordingly, disease states in which the, ICE inhibitors of formula (I) may be useful as therapeutic agents include, but are not limited to, peptic shock, inflammatory conditions such as rheumathoid arthritis, colitis, hepatitis, glomerulonephritis, myocarditis, etc.

The following examples are illustrating but not limiting the scope of the invention. The $R_f$ values recorded in the examples were determined by thin-layer chromatography, using silica gel as adsorbent (DC-Alufolien Kieselgel 60 $F_{254}$, Merck, Darmstadt), in the following developing solvents:
1. Ethyl acetate
2. Ethyl acetate-hexane (1:2)
3. Ethyl acetate-pyridine-acetic acid-water (960:20:6:11)
4. Ethyl acetate-pyridine-acetic acid-water (480:20:6:11)
5. Ethyl acetate-pyridine-acetic acid-water (240:20:6:11)
6. Ethyl acetate-pyridine-acetic acid-water (120:20:6:11)
7. Ethyl acetate-pyridine-acetic acid-water (60:20:6:11)
8. Chloroform-acetic acid (95:5)
9. Chloroform-acetone (95:5)

The capacity factors (k') specified in the examples were determined with the apparatus "Pharmacia LKB analytical HPLC System Two" as follows:
Column: VYDAC C-18 reversed phase: 10 µm, 300 Å, 4×250 mm.
Buffer A: 0.1 % trifluoroacetic acid in water.
Buffer B: 0.1 % trifluoroacetic acid in acetonitriie.
Gradients applied at 1 ml/min flow rate,
0–30 min. 0–60 % buffer B.

Detection of peptide content of the eluates was performed by UV light at 214 nm. Sample concentration was 1 mg/ml buffer A, injection volume 25 µl.

The FAB mass spectra were recorded in a Finnigan MAT 8430 apparatus at a resolution of 1250. Parameters: voltage of ion accelerator 3 kV, temperature of ion source 25° C., matrix m-nitrobenzylalcohol, FAB gas xenon and FAB accelerator voltage 9 kV.

The ESI positive ionisation measurements were performed in a VG, Quattro 4000 (Fisons Instrument) apparatus. The samples were dissolved in a mixture of acetonitrile—water (1:1) containing 0.1% of formic acid and were introduced with a 50 µl samnple-loop into the ion source at a carrier solvent flow rate of 81–100 µl/min. Parameters: voltage of ion accelerator 50 V, capillary potential 3.53 kV, temperature of ion source 100–120° C., conus potential 35.0 V, ion energy 2.6 V, resolution (small/large masses) 14.0/14.2, data collection disk (16 point/Da).

NMR spectra were obtaine d with a Bruker AC250 spectrometer. Chemical shifts are recorded on a $\delta(\delta_{TMS}=0_{ppm})$ scale.

The specific rotations ($[\alpha]_D$) were determined at 20° C.

EXAMPLE 1

(3R) -(Acetyl-L-tyosyl-L-valyl-L-alanylamino)-4-carboxybutyraidehyde

Step 1: (3R)-3-(Acetyl-L-tyrosyl-L-valyl-L-alanylaminol-4-t-butoxycarbonyl-butyraldehyde Diethyl Acetal 0.2 g (0.5 mmol) of acetyl-L-tyrosyl-L-valyl-L-alanine (Example 1, Step A5) and 0.13 g (0.5 mmol ) of (3R)-3-(amino)-4-t-butoxycarbonyl-butyraidehyde diethyl acetal (Example 1, Step B4), furthermore 0.08 g (0.52 mmol) of N-hydroxy-benzotriazole are dissolved in 2 ml of dimethylformamide, then 0.1 g (0.52 mmol) of dicyclohexylcarbodiimide is added at 0° C. The reaction mixture is stirred for one hour at 0° C. then for 5 hours at room temperature. The precipitated dicyclohexylurea is filtered, washed with 2×0.5 ml of dimethylformamide, then the filtrate is evaporated at a pressure of 2.0–2.5 kPa. The residue is dissolved in 10 ml of ethyl acetate, washed neutral first with 3 ml of 5% $NaHCO_3$ then with water, finally the solution is dried over anhydrous sodium sulfate and evaporated at a pressure of 2.0–2.5 kPa. The solid residue is rubbed with diethyl ether, filtered, washed with diethyl ether and dried in a vacuum desiccator.

Yield: 0.22 g (35 mmol, 74%). $R_f(5)$=0.65.

The ESI mass spectrum (637 $[M+H]^+$) confirms the expected structure.

Step 2: (3R)-3-Acetyl-L-tyrosyl-L-valyl-L-alanylamino)-4-carboxybutyraldehyde 0.18 g (0,29 mmol) of the protected peptide aldehyde (Example 1, Step 1) is dissolved in 2 ml of trifluoroacetic acid and left to stand at room temperature for 2 hours, then the mixture is diluted with 10 ml of diisopropyl ether and left to stand in the refrigerator for 3 hours. The formed precipitate is filtered, washed with diisopropyl ether and dried in a vacuum desiccator.

Yield: 0.14 g (95%). $R_f(5)$=0.15. HPLC: k'=2.75.

The FAB mass spectrum (507 $[M+H]^+$) confirms the expected structure.

$^1$H NMR (250 MHz, DMSO-$d_6$): δ 12.30 (br, 1H, COOH); 9.60 (t, 1H, HC=O); 9.15 (s, 1H, Ar—OH); 8.10–8.00 (m, 3H, 3×NH); 7.82 (d, 1H, NH); 7.08 (dm, 2H, ArH); 6.65 (dm, 2H, ArH); 4.50 (m, 2H, 2×NCH); 4.10 (m, 2H, 2×NCH); 3.00–2.40 (m, 4H, 2×$CH_2$); 1.30 (m, 1H, CH); 1.25 (d, 3H, $CH_3$); 0.90 (d, 3H, $CH_3$); 0.88 (d, 3H, $CH_3$).

The starting materials can be prepared as follows:

Compound A

Acetyl-L-tyrosyl-L-valyl-L-alanine

Step A1: Methyl L-valyl-L-alaninate Hydrogen Oxalate 2.69 g (8.0 mmol) of methyl benzyloxycarbonyl-L-valyl-L-alaninate [E. Klieger and E. Schröder: Ann. Chem. 661, 193 (1963)] are dissolved in 25 ml of methanol, 0.72 9 (8.0 mmol) of anhydrous oxalic acid and 0.1 g of Pd/C catalyst are added, then the mixture is submitted to hydrogenation at about 20° C. The catalyst is filtered off and the filtrate is evaporated at a pressure of 2.0–2.5 kPa. The crystalline residue is rubbed with diethyl ether, filtered, washed with diethyl ether and dried in a vacuum desiccator.

Yield: 2.2 g (7.5 mmol, 93.75%). $R_f(7)$=0.50. M. p.: 156–158° C.

Step A2: Methyl Benzyloxycarbonyl-L-tyrosyl-L-valyl-L-alaninate 2.04 g (7.0 mmol) of methyl L-valyl-L-alaninate hydrogen oxalat (Example 1, Step 1A) are suspended in 10 ml of dimethylformamide, then 1.96 ml (14 mmol) of triethylamine and 3.45 g (7.0 mmol) of benzyloxycarbonyl-L-tyrosine 2,4,5-trichlorophenyl ester are added. The reaction mixture is stirred for 16 hours at room temperature, then it is evaporated at a pressure of 2.0–2.5 kPa. The residue is dissolved in 30 ml of ethyl acetate, the solution is washed with 3×10 ml of water, 10 ml of 5% of $NaHCO_3$ and 3×10 ml of water, then dried over anhydrous sodium sulfate and evaporated at a pressure of 2.0–2.5 kPa. The gelatinous residue is rubbed with diethyl ether, filtered, washed with diethyl ether and dried in a vacuum desiccator.

Yield: 3.16 9 (6.33 mmol, 90%). $R_f(3)$=0.70. M. p.: 179–181° C. $[\alpha]_D$=−32.5° (c=0.5, methanol).

Step A3: Methyl L-tyrosyl-L-valyl-L-alaninate 2.99 g (6.0 mmol) of methyl benzyloxycarbonyl-L-tyrosyl-L-valyl-L-alaninate (Example 1, Step A2) are dissolved in 30 ml of dimethylformamide, 0.2 g of Pd/C catalyst is added, then the mixture is submitted to hydrogenation at about 20° C. The catalyst is filtered off and the filtrate is evaporated at a pressure of 2.0–2.5 kPa. The residue is rubbed with diethyl ether, filtered, washed with diethyl ether and dried in a vacuum desiccator.

Yield: 1.81 g (4.9 mmol, 82%). $R_f(6)$=0.50.

The product is directly used in the next acylating step.

Step A4: Methyl Acetyl-L-tyrosyl-L-valyl-L-alaninate 0.73 g (2.0 mmol) of methyl L-tyrosyl-L-valyl-L-alaninate (Example 1, Step A3) is dissolved in 5 ml of dimethylformamide, then 0.4 g (2.2 mmol) of p-nitrophenyl-acetate is added. The reaction mixture is stirred at room temperature overnight then is evaporated at a pressure of 2.0–2.5 kPa. The residue is dissolved in 15 ml of ethyl acetate, the solution is washed with 3×5 ml of water, 5 ml of 1 M $KHSO_4$ and 3×5 ml of water, then dried over anhydrous sodium sulfate and evaporated at a pressure of 2.0–2.5 kPa. The residue is rubbed with diethyl ether, filtered, washed with diethyl ether and dried in a vacuum desiccator.

Yield: 0.66 g (1.62 mmol, 81%). $R_f(5)$=0.30. M. p.: 193–195° C.

Step A5: Acetyl-L-tyrosyl-L-valyl-L-alanine 0.60 g (1.47 mmol) of methyl acetyl-L-tyrosyl-L-valyl-L-alaninate (Example 1, Step A4) is dissolved in 10 ml of acetone and saponified with 1 M sodium hydroxide in the presence of thymolphthalein indicator. The acetone is distilled off from the reaction mixture at a pressure of 2.0–2.5 kPa, then 2 ml of water are added and the mixture is extracted with 3 ml of diethyl ether. The aqueous layer is acidified with 1 M $KHSO_4$ to pH=3, saturated with solid sodium chloride and extracted with 3×5 ml of ethyl acetate. The pooled ethyl acetate extracts are washed with 3 ml of 15% NaCl solution, dried over sodium sulfate and evaporated at a pressure of 2.0–2.5 kPa. The residue is rubbed with diethyl ether, filtered, washed with diethyl ether and dried in a vacuum desiccator.

Yield: 0.37 g (1.0 mmol. 63%). $R_f(6)$=0.40. M. p.: 245–247° C. $[\alpha]_D$=−21.9° (c=1, methanol). Analysis for $C_{19}H_{27}N_3O_6$ (393.43) Calculated: C %=58.00; H %=6.92; N %=10.68. Found: C %=57.35; H %=6.95; N %=10.3.

Compound B (3R)3-Amino-4-t-butoxycarbonyl-butyraldehyde Diethyl Acetal

Step B1: (3R)-3-(Benzyloxycarbonylamino)-4-t-butoxycarbonyl-butyric Acid Dicyclohexyl Ammonium Salt 12.6 g (25 mmol) of N-benrzyloxycarbonyl-4-t-butyl-L-aspartic acid dicyclohexyl ammonium salt are dissolved in 75 ml of ethyl acetate and 27.5 ml of 1 M $KHSO_4$ solution. The phases are separated, the ethyl acetate phase is washed neutral with water, then dried over anhydrous sodium sulfate and evaporated at a pressure of 2.0–2.5 kPa. The residue is dissolved in 50 ml of tetrahydrofuran, cooled to −15° C., then under constant stirring 2.8 ml (25 ml) of N-methyl-morpholine and 3.3 ml (25 mmol) of isobutyl chloroformate are added. After stirring for 5 minutes the reaction mixture is diluted with 30 ml of diethyl ether, the precipitated salts are filtered and washed with 2×10 ml of diethyl ether. Then 30 mmol of diazomethane in diethyl ether solution are added to the filtrate, the reaction mixture is left to stand for one hour at 0° C., thereafter washed with 2×30 ml of water, dried over sodium sulfate and evaporated at a pressure of 2.0–2.5 kPa. The residual oil—N-benzyloxycarbonyl-4-t-butyl-L-aspartyl-diazomethane [$R_f(3)$=0.80]—is dissoved in 50 ml of anhydrous methanol and refluxed after the addition of 0.58 g (2.5 mmol) of silver oxide for 8 hours. The mixture is left to cool, filtered over a carbon layer and evaporated at a pressure of 2.0–2.5 kPa. The residue is subjected to column chromatography on silica gel using a developing solvent of ethyl acetate—n-hexane (2:3). The fractions with Rf(2)= 0.50 are pooled and evaporated at a pressure of 2.0–2.5 kPa. The residue is dissolved in 40 ml of acetone and saponified with 1 M sodium hy:droxide in the presence of thymolphthalein indicator. At the conclusion of the reaction, the solution is neutralized with 1 M $KHSO_4$ and the acetone is evaporated at reduced presure. First the aqueous solution is made alkaline, extracted with 30 ml of diethyl ether, then acidified with 1 M $KHSO_4$ to pH=3 and extracted with 3×20 ml of ethyl acetate. The ethyl acetate solutions are pooled, dried over sodium sulfate and evaporated at a pressure of 2.0–2.5 kPa. The residue is dissolved in 30 ml of diethyl ether, then 4.95 ml (25 mmol) of dicyclohexylamine are added. The precipitated salt is filtered, washed with diethyl ether and dried in a vaccuum desiccator.

Yield: 7.88 g (15.2 mmol, 61%). $R_f(1)$=0.60. M. p.: 108–110° C. $[\alpha]_D$=−3.2° (c=1, methanol). Analysis for $C_{29}H_{46}N_2O_6$ (518.68) Calculated: C %=67.15; H %=8.93; N %=5.4. Found: C %=67.2; H %=9.0; N %=5.2.

$^1$H NMR (250 MHz, DMSO-$d_6$): δ 7.35 (m, 5H, ArH); 5.00 [dd (AB); 2H, $OCH_2$]; 4.8 (m, 1H, NCH); 2.82 [m, 2H, NCH (DCHA)]; 2.50–2.10 (m, 4H, 2×$CH_2$); 2.00–1.00 [m, 20H, 10×$CH_2$ (DCHA)]; 1.38 [s, 9H, $(CH_3)_3$].

Step B2: (3R)-34Benzyloxycarbonylamino)-4-t-butoxycarbonyl-butync Acid 3,5-Dimethylpyrazolide 5.2 g (10 mmol) of (3R)-3-(benzylcxycarbonylamino)-4-t-butoxycarbonyl-butyric acid dicyclohexyl ammonium salt (Example 1, Step B1) are dissolved in 30 ml of ethyl acetate and 11 ml of a 1 M $KHSC_4$ solution. The layers are separated, the ethyl acetate layer is washed neutral with water, dried over sodium sulfate and evaporated at a pressure of 2.0–2.5 kPa. The residue is dissolved in 10 ml of tetrahydrofuran, the solution is chilled to −20° C., then under constant stirring 1.11 ml (10 mmol) of N-methyl-morpholine and 1.32 ml (10 mmol) of isobutyl chloroformate are added. The mixture is stirred for 10 minutes, then 0.96 g (10 mmol)

of 3,5-dimethylpyrazole, dissolved in 10 ml of tetrahydrofuran, is introduced. The reaction mixture is stirred for 30 minutes at −10° C., then for one hour at 0° C. The salts are filtered off and the filtrate is evaporated at a pressure of 2.0–2.5 kPa. The residue is dissolved in 30 ml of ethyl acetate, the solution is washed with 3×10 ml of water, 10 ml of 1 M KHSO$_4$, 3×10 ml of water, 10 ml of 5% NaHCO$_3$ and 3×10 ml of water, dried over anhydrous sodium sulfate and evaporated at a pressure of 2.0–2.5 kPa. The obtained 3.33 g of oil (8.0 mmol) is assumed to be the desired product [R$_f$(1)=0.80] which is directly used in the following step.

$^1$H NMR (250 MHz, CDCl$_3$): δ 7.25 (m, 5H, ArH); 5.90 (s, 1H, =CH); 5.80 (d, 1H, NH); 4.50 (m, 1H, NCH); 3.48 (dd, 1H, OC—CH$_s$); 3.33 (dd, 1H, OC—CH$_b$); 2.62 (m, 2H, CH$_2$); 2.47 (s, 3H, CH$_3$); 2.19 (s, 3H, CH$_3$); 1.40 [(s, 9H, (CH$_3$)$_3$].

Step B3: (3R)-3-(Benzyloxycarbonylamino)-4-t-butoxycarbonyl-butyraldehyde Diethyl Acetal 3.12 g (7.5 mmol) of (3R)-3-(benzyloxycarbonylamino)-4-tbutoxycarbonyl-butyric acid 3,5dimethylpyrazolide (Example 1, Step B2) are dissolved in 20 ml of tetrahydrofuran and under stirring, at −30° C. a solution of 7.5 mmole of lithium aluminum hydride in tetrahydrofuran is added. The reaction mixture is stirred for 30 min, then the mixture is acidified under chilling and stirring to pH=3 with 1 M KHSO$_4$, diluted with 50 ml of ethyl acetate, washed with 3×10 ml of water, dried over anhydrous sodium sulfate and evaporated at a pressure of 2.0–2.5 kPa. The residual oil [R$_f$(2)=0.35 (aldehyde) and 0.20 (3,5-dimethylpyrazolel is dissolved in 3 ml of methanol, then a solution of 1.17 g (11.25 mmol) of sodium hydrogen sulfite in 15 ml of water is added. The solution is stirred for one hour, then extracted with 3×5 ml of diethyl ether. 1.6 g (15 mmol) of sodium carbonate and 10 ml of ethyl acetate are added to the washed aqueous phase and stirring is continued for further 2 hours. The phases are separated, the ethyl acetate phase is washed with water, dried over anhydrous sodium sulfate and evaporated at a pressure of 2.0–2.5 kPa. The residue is 2.07 g (6.46 mmol) of pure aldehyde [R$_f$(2)=0.35)] which is dissolved in 10 ml of anhydrous ethanol, then 6.64 ml (40 mmol) of triethyl orthoformate and 3 drops of trifluoroacetic acid are added and the mixture is left to stand for 3 days at room temperature. The reaction mixture is diluted with 20 ml of n-hexane and 20 ml of water, the organic layer is washed with 3×10 ml of 5% NaHCO$_3$ and 3×10 ml of water, dried over anhydrous sodium sulfate and evaporated at a pressure of 20–2.5 kPa.

Yield: 2.6 g (6.6 mmole, 88%). R$_f$(2)=0.60.

The FAB mass spectrum (396[M+H]$^+$) confirms the assumed structure.

$^1$H NMR (250 MHz, DMSO-d$_6$): δ 7.38 (m, 5H, ArH); 7.24 (d, 1H, NH); 5.00 (s, 2H, OCH$_2$); 3.90 (m, 1H, NCH); 3.60–3.45 (m, 4H, OCH$_2$); 2.32 (dd, 2H, CH$_2$); 1.65 (t, 2H, CH$_2$); 1.36 [s, 9H, (CH$_3$)$_3$; 1.08 (t, 3H, CH$_3$); 1.07 (t, 3H, CH$_3$).

Step B4: (3R)-3-Amino-4-t-butoxycarbonyl-butyraldehyde Diethyl Acetal 2.56 g (6.5 mmol) of (3R)-3-(benzyloxycarbonylamino)-4-tbutoxycarbonyl-butyraldehyde diethyl acetal (Example 1, Step B3) are dissolved in 10 ml of ethanol and the solution is hydrogenated at about 20° C. in the presence of 0.20 g of Pd/C catalyst. The catalyst is filtered off and the filtrate is evaporated at a pressure of 2.0–2.5 kPa. The residue, 1.7 g (6.5 mmol) of an oil [R$_f$(5)=0.25], is assumed to be the target product and is directly used in the coupling reaction.

The FAB mass spectrum (262 [M+H]$^+$) confirms the assumed structure.

EXAMPLE 2

(3R)-3-(Ethoxycarbonyl-L-alanyl-L-tyrosyl-L-valyl-L-alanylamino)-4-carboxybutyraldehyde (SEQ ID NO:1)

Step 1: (3R)-3-(Ethoxycarbonyl-L-alanyl-L-tyrosyl-L-valyl-L-alanylamino)-4-t-butoxycarbonyl-butyraldehyde Diethyl Acetal (SEQ ID NO:1)

Starting from 0.25 g (0.5 mmol) of ethoxycarbonyl-L-alanyl-L-tyrosyl-L-valyl-L-alanine (Example 2, Step A4) and 0.13 g (0.5 mmol) of (3R)-3-amino-4-t-butoxycarbonyl-butyraldehyde diethyl acetal (Example 1, Step B4), and using proportional amounts of reagents and solvents, the corn ponents are coupled and the end product isolated according to the procedure described in Example 1, Step 1.

Yield: 0.32 g (0.43 mmol, 85%). R$_f$(5)=0.70.

The ESI mass spectrum (738 [M+H]$^+$) confirms the assumed structure.

Step 2: (3R)-3-(Ethoxycarbonyl-L-alanyl-L-tyrosyl-L-valyl-L-alanylamino)-4-carboxybutyraldehyde (SEQ ID NO:1)

0.22 g (0.3 mmol) of the protected peptide-aldehyde (Example 2, Step 1) is transformed according to the procedure described in Example 1, Step 2, using proportional amounts of reagents and solvents.

Yield: 0.17 9 (95%). R$_f$(5)=0.25. HPLC: k'=4.11

The FAB and ESI mass spectra (608 [M+H]$^+$) confirm the assumed structure.

$^1$H NMR (250 MHz, DMSO-d$_6$): δ 12.5 (br, 1H, COOH); 9.60 (s, 1H, HC=O); 9.15 (br, 1H, Ar—OH); 8.02 (d, 1H, NH); 8.00 (d, 1H, NH); 7.30 (d, 1H, NH); 7.05 (dm, 2H, ArH); 6.63 (dm, 2H, ArH); 4.50 (m, 1H, NCH); 4.19 (m, 1H, NCH); 4.00 (q, 2H, OCH$_2$); 3.50 (m, 3H, 3×NCH); 1.19 (d, 6H, 2×CH$_3$); 1.17 (d, 3H, CH$_3$); 1.07 (d, 3H, CH$_3$); 0.88 (t, 3H, CH$_3$).

The starting materials can be prepared as follows.

Compound A

Ethoxycarbonyl-L-alanyl-L-tyrosyl-L-valyl-L-alanine (SEQ ID NO:1)

Step A1: Ethoxycarbonyl-L-alanine Cyclohexyl Ammonium Salt 0.89 g (10 mmol) of L-alanine is dissolved in 30 ml of a mixture of dioxanelwater (2:1), then 20 ml of 1 M sodium hydroxide are added and the mixture is cooled to 0° C. 0.96 ml (10 mmol) of ethyl chloroformate is introduced dropwise with constant stimng. After stirring for one hour the dioxane is distilled off at a pressure of 2.0–2.5 kPa, the residue is extracted with 10 ml of diethyl ether, acidified with 1 M KHSO$_4$ to pH=3, then the mixture is extracted with 3×10 ml of ethyl acetate. The pooled ethyl acetate extracts are washed with 2×10 ml of water, dried over anhydrous sodium sulfate and evaporated at a pressure of 2.0–2.5 kPa. The residue is dissolved in 10 ml of diethyl ether and 1.37 ml (12 mmol) of cyclohexylamine are added. The formed crystals are filtered, washed with diethyl ether and airried.

Yield: 1.54 g (5.92 mmol, 59%). R$_f$(5)=0.60. M. p.: 115–116° C. [α]$_D$=+1° (c=1, methanol). Analysis for C$_{12}$H$_{24}$N$_2$O$_4$ (260.328) Calculated: C %=55.36; H %=9.29; N %=10.76. Found: C %=55.2; H %=9.4; N %=10.65.

Step A2: Pentachlorophenyl Ethoxycarbonyl-L-alaninate 2.6 g (10 mmol) of ethoxycarbonyl-L-alanine cyclohexyl ammonium salt (Example 2, Step A1) are dissolved in 30 ml of ethyl acetate and 12 ml of 1 M KHSO$_4$. The phases are separated, the ethyl acetate phase is washed neutral with water, dried over anhydrous sodium sulfate and concentrated at a pressure of 2.0–2.5 kPa to about 15 ml. The concentrate is cooled to 0° C. and under stirring 2.93 g (11 mmol) of pentachlorophenol and 2.26 g (11 mmol) of dicyclohexyl-carbodiimide are added, then the reaction mixture is left to stand for 16 hours. The precipitated dicyclohexylurea is filtered off and the filtrate is evaporated at a pressure of 2.0–2.5 kPa. The residue is rubbed with diisopropyl ether, filtered, washed with diisopropyl ether and dried in a vacuum desiccator.

Yield: 3.3 g (8.06 mmol, 80%). $R_f(9)=0.75$. M. p.: 154–155° C. $[\alpha]_D=43.56°$ (c=1, methanol). Analysis for $C_{12}H_{10}NO_4Cl_5$ (409.493) Calculated: C %=35.19; H %=2.46; N %=3.42; Cl %=43.29. Found: C %=35.2; H %=2.5; N %=3.4; Cl %=43.3.

Step A3: Methyl Ethoxycarbonyl-L-alanyl-L-tyrosyl-L-valyl-L-alaninate (SEQ ID NO:1)

0. 91 g (2.5 mmol) of methyl L-tyrosy-L-valyl-L-alaninate (Example 1, Step A3) is dissolved in 4.0 ml of dimethylformamide, then 1.02 g (2.5 mmol) of pentachlorophenyl ethoxycarbonyl-L-alaninate (Example 2, Step 2A) and 0.28 ml (2.5 mmol) of N-methyl-morpholine are added. The reaction mixture is left to stand overnight, thereafter it is evaporated at a pressure of 2.0–2.5 kPa. The gelatinous residue is rubbed with ethyl acetate, the obtained precipitate is filtered, washed with ethyl acetate and dried in a vacuum desiccator.

Yield: 1.09 g (2.15 mmol, 89%). $R_f(5)=0.55$. M. p.: 189–193° C. $[\alpha]_D=-58.65°$ (c=0.5, methanol).

Step A4: Ethoxycarbonyl-L-alanyl-L-tyrosyl-L-valyl-L-alanine (SEQ ID NO:1)

0.94 g (1.85 mmol) of methyl ethoxycarbonyl-L-alanyl-L-tyrosyl-L-valyl-L-alaninate (Example 2, Step A3) is transformed according to the method described in Example 1, Step A5, using proportional amounts of reagents and solvents.

Yield: 0.8 g (1.62 mmol, 87%). $R_f(5)=0.30$. M. p.: 214–216° C. $[\alpha]_D=-54.5°$ (c=0.5, methanol).

The ESI mass spectrum (495 [M+H]$^+$) confirms the assumed structure

Analysis for $C_{23}H_{34}N_4O_8$ (494.534) Calculated C %=55.86; H %=6.93; N %=11.33. Found: C %=55.3; H %=6.95; N %=10.8.

EXAMPLE 3

(3R)-3-(Ethoxycarbonyl-L-tyrosyl-L-isoleucyl-L-alanylamino)-4-carboxybutyraldehyde Step 1: (3R)-3-(Ethoxycarbonyl-L-tyrosyl-L-isoleucyl-L-alanylamino)-4-t-butoxycarbonyl-butyraldehyde-diethyl Acetal Starting from 0.22 g (0.5 mmol) of ethoxycarbonyl-L-tyrosyl-L-isoleucyl-L-alanine (Example 3, Step A6) and 0.13 g (0.5 mmol) of (3R)-3-amino-4-t-butoxycarbonyl-butyraidehyde diethyl acetal (Example 1, Step B4) and using proportional amounts of reagents and solvents, the components are coupled and the end product isolated according to the process described in Example 1, Step A1.

Yield: 0.25 g (0.36 mmol, 73%). M. p.: 159–163° C. $R_{(f)}(1)=0.55$.

The ESI mass spectrum (681 [M+H]$^+$) confirms the assumed structure.

Step 2: (3R)-3-Ethoxycarbonyl-L-tyrosyl-L-isoleucyl-L-alanylamino)-4-carboxybutyraldehyde 0.20 g (0.3 mmol) of the protected peptide-aldehyde (Example 3, Step 1) is transformed according the procedure described in Example 1, Step 2, using proportional amounts of reagents and solvents.

Yield: 0.14 g (0.25 mmol, 87%). $R_f(4)=0.20$ HPLC: k'=4.65

The FAB and ESI mass spectra (551 [M+H]$^+$) confirm the assumed structure.

$^1$H NMR (250 MHz, DMSO-d$_6$): δ 12.30 (br, 1H, COOH); 9.60 (br, 1H, HC=O); 9.20 (br, 1H, Ar—OH); 8.02 (d, 1H, NH); 8.00 (d, 1H, NH); 7.83 (d, 1H, NH); 7.20 (d, 1H, NH); 7.12 (dm, 2H, ArH); 6.66 (dm, 2H, ArH); 4.40 (m, 1H, NCH); 4.10 (m, 4H, 2×NCH, OCH$_2$); 3.92 (m, 1H, NCH); 3.00–2.40 (m, 4H, 2×CH$_2$); 1.90–1.00 (m, 5H, 2×CH$_2$, CH); 1.15 (d, 6H, 2×CH$_3$); 0.9 (d, t, 6H, 2×CH$_3$).

The starting materials can be prepared as follows.

Compound A

Ethoxycarbonyl-L-tyrosyl-L-isoleucyl-L-alanine

Step A1: Methyl Ethoxycarbonyl-L-tymsinate 11.6 g (50 mmol) of methyl L-tyrosinate hydrochloride [E. Schroder. Ann. Chem. 692, 241 (1966)] are dissolved in 100 ml of chloroform and 50 ml of 1 M NaHCO$_3$. The biphasic system is cooled to 0° C., then under constant stirring, dropwise, 4.2 ml (55 mmol) of ethyl chloroformate and, 55 ml of 1 M NaHCO$_3$ are added. The reaction mixture is stirred for one hour at 0° C., then for another hour at room temperature. The phases are separated and the aqueous phase is washed with 50 ml of chloroform. The pooled chloroform solutions are washed with 0.5 M HCl and 3×20 ml of water, dried over anhydrous sodium sulfate and evaporated at a pressure of 2.0–2.5 kPa. The residue is 9.9 g (37 mmol) of an oil [$R_f(3)=0.86$] asumed to be the target product which is used directly in the next step.

Step A2: Ethoxycarbonyl-L-tyrosine Cyclohexyl Ammonium Salt

Methyl ethoxycarbonyl-L-tyrosinate, obtained in Step A1, is dissolved in 50 ml of methanol andaponified in the presence of thymolphthalein indicator with 2 M sodium hydroxide. At the conclusion of the reaction [$R_f(3)=0.30$] the methanol is distilled off at a pressure of 2.0–2.5 kPa. The residual aqueous solution is washed with 2×10 ml of ethyl acetate, then acidified to pH=3 with 3 M hydrochloric acid. The separated oil is extracted with 3×20 ml of ethyl acetate. The pooled ethyl acetate solutions are washed neutral with water, dried over anhydrous sodium sulfate and evaporated at a pressure of 2.0–2.5 kPa. The residue is dissolved in 40 ml of diisopropyl ether, and then 4.57 ml (40 mmol) of cyclohexylamine are added. The precipitated crystals are filtered, washed with diisopropyl ether and air-dried.

Yield: 12.52 9 (35.5 mmol, 96%). $R_f(3)=0.30$. M. p.: 173–180° C. $[\alpha]_D=+40.4°$ (c=1, methanol). Analysis for $C_{18}H_{28}N_2O_5$ (352.437) Calculated: C %=61.34; H %=8.01; N %=7.95. Found: C %=61.5; H %=8.0; N %=7.7.

Step A3: Methyl Benzyloxycarbonyl-L-isoleucyl-L-alaninate 13.4 9 (30 mmol) of benzyloxycarbonyl-L-isoleucine 2,4, 5-trichlorophenyl ester [J. Pless and R. A. Boissonas: Helv. Chim. Acta 46, 1609 (1963)] are dissolved in 30 ml of dimethylfornamide, then 4.17 g (30 mmal) of methyl L-alaninate hydrochloride (S. Goldschmidt and K. K Gupta: Chem. Ber. 98, 2831 (1965)] and 4.2 ml (30 mmol) of triethylamine are added. The reaction mixture is left to stand at room temperature overnight, then evaporated at a pressure of 2.0–2.5 kPa. The residue is dissolved in 60 ml of ethyl acetate, extracted with 3×10 ml of 1 M hydrochloric acid, 3×10 ml of water, 3×10 ml of 5% NaHCO$_3$ solution and 3×10 ml of water, dried over anhydrous sodium sulfate and evaporated at a pressure of 2.0–2.5 kPa. The residue is rubbed with diethyl ether, filtered, washed with diethyl ether and dried in a vacuum desiccator.

Yield: 8.4 g (24 mmol, 80%). $R_f(5)=0.83$. M. p.: 174–175° C. $[\alpha]_D=45.7°$ (c=1, methanol).

Step A4: Methyl L-isoleucyl-L-alaninate Oxalate 7.45 g (21.3 mmol) of methyl benzyloxycarbonyl-L-isoleucyl-L-alaninate (Example 3, Step A3) is dissolved in 140 ml of methanol, then 1.9 g (21.3 mmol) of oxalic acid are added and the mixture is hydrogenated in the presence of 0.3 g of Pd/C catalyst. At the conclusion of the reaction $[R_f(7)=0.3]$ the catalyst is filtered off and the filtrate is evaporated at a pressure of 2.0–2.5 kPa. The residue is crystallyzed with diethyl ether, the crystals are filtered, washed with diethyl ether and dried in a vacuum desiccator.

Yield: 5.57 g (18.2 mmol, 85%). $R_f(7)=0.30$.

Recrystallyzing 1.0 g of substance from a mixture of 2 ml of methanol and 20 ml of diethyl ether yields 0.7 g of product.

$[\alpha]_D=-7.46°$ (c=1, methanol). Analysis for $C_{12}H_{22}N_2O_7 \cdot \frac{1}{2}H_2O$ (315.320) Calculated: C %=45.70; H %=7.35; N %=8.88. Found: C %=45.8; H %=7.9; N %=8.8.

Step A5: Methyl Ethoxycarbonyl-L-tyrosyl-L-isoleucyl-L-alaninate 1.8 g (5 mmol) of ethoxycarbonyl-L-tyrosine cyclohexyl-ammonium salt (Example 3, Step A2) are dissolved in 20 ml of ethyl acetate and 6 ml of 1 M $KHSO_4$. The phases are separated, the ethyl acetate phase is washed neutral with water, dried over anhydrous sodium sulfate and evaporated at a pressure of 2.0–2.5 kPa. The residue is dissolved in 5 ml of dimethylformamide, chilled to −15° C. and under constant stirring 0.55 ml (5 mmol) of N-methyl-morpholine and 0.66 ml of isobutyl chlorofomnnate are added. After 10 min. the following solution chilled to −15° C. is added: 1.5 g (5 mmol) of methyl L-isoleucyl-L-alaninate oxalate (Example 3, Step A4) and 1.4 ml (10 mmol) of triethylamine in 5 ml of dimethylformamide. The reaction mixture is stirred under cooling for 30 min, then at room temperature for further 30 min, then it is filtered and evaporated at a pressure of 2.0–2.5 kPa. The residue is dissolved in 30 ml of ethyl acetate, washed with 2×10 ml of 1 M $KHSO_4$ and 2×10 ml of water, and evaporated at 2.0–2.5 kPa. The residue is crystallyzed with diethyl ether, filtered, washed with diethyl ether and dried in a vacuum desiccator.

Yield: 2.2 g (4.88 mmol, 97%). $R_f(5)=0.74$. M. p.: 210–212° C.

Step A6: Ethoxycarbonyt-L-tyrosyl-L-isoleucyl-L-alanine 1.8 g (4 mmol) of methyl ethoxycarbonyl-L-tyrosyl-L-isoleucyl-L-alaninate (Example 3, Step A5) is dissolved in 30 ml of methanol and saponified with 2 M sodium hydroxide in the presence of thymolphthalein indicator. The reaction mixture is concentrated to 5–10 ml at a pressure of 2.0–2.5 kPa, diluted with 20 ml of water and extracted with 2×5 ml of ethyl acetate. The aqueous solution is acidified with 1 M $KHSO_4$ to pH=3 and extracted with 3×20 ml of ethyl acetate. The ethyl acetate solutions are pooled, washed neutral with water, dried over anhydrous sodium sulfate and evaporated at a pressure of 2.0–2.5 kPa. The residue is crystallyzed with diethyl ether, filtered, washed with diethyl ether and dried in a vacuum desiccator.

Yield: 1.35 g (3.08 mmol, 77%). $R_f(5)=0.37$. M. p.: 213–219° C. $[\alpha]_D=-28.4°$ (c=1, methanol). Analysis for $C_{21}H_{31}N_3O_7$ (437.482) Calculated: C %=57.65; H %=7.14; N %=9.60. Found: C %=57.3; H %=7.15; N %=9.3.

EXAMPLE 4

(3R)-3-(L-Lactyl-L-tyrosyl-L-valyl-L-alanylamino)-4-carboxybutyr-aldehyde

Step 1: (3R)-3-(O-tetrahydropyranyl)-L-lactyl-L-tyrosyl-L-valyl-L-alanylamino)-4-t-butoxycarbonyl-butyraldehyde Diethyl Acetal 0.25 g (0.5 mmol) of O-tetrahydropyranyl-L-lactyl-L-tyrosyl-L-valyl-L-alanine (Example 4, Step A5), 0.13 g (0.5 mmol) of (3R)-3-amino-4-t-butoxycarbonyl-butyraldehyde diethyl acetal (Example 1, Step B4) and 0.08 g (0.52 mmol) of N-hydroxy-benzotriazole are dissolved in 2 ml of dimethylformamide, then 0.1 g (0.52 mmol) of dicyclohexylcarbodiimide is added at 0° C. The reaction mixture is stirred for one hour at 0° C., then for 5 hours at room temperature. The precipitated dicyclohexylurea is filtered, washed with 2×0.5 ml of dimethylformamide and the filtrate is evaporated at a pressure of 2.0–2.5 kPa. The residue is dissolved in 10 ml of ethyl acetate, washed neutral with 3 ml of 5% $NaHCO_3$ solution, then with water, dried over anhydrous sodium sulfate and evaporated at a pressure of 2.0–2.5 kPa. The residue is dissolved in 0.5–1.0 ml of ethyl acetate and subjected to chromatography on a silica gel column using ethyl acetate as eluant The fractions containing the pure main product are pooled and evaporated at a pressure of 2.0–2.6 kPa. The residue is rubbed with petroleum ether, filtered, washed with petroleum ether and dried in a vacuum desiccator.

Yield: 0.20 g (0.26 mmol, 52%): $R_f(1)=0.55$.

The FAB mass spectrum (751 $[M+H]^+$) confirms the assumed structure.

Step 2: (3R)-3-(L-Lactyl-L-tyrosyl-L-valyl-L-alanylamino)-4-carboxybutyraldehyde 0.10 g (0.13 mmol) of the protected peptide aldehyde (Example 4, Step 1) is dissolved in 2 ml of trifluoroacetic acid and left to stand at room temperature for 2 hours. Then the mixture is diluted with 10 ml of diisopropyl ether and left in the refrigerator for 3 hours. The precipitated solid is filtered, washed with diisopropyl ether and dried in a vacuum desiccator.

Yield: 0.06 g (0.11 mmol). $R_f(6)=0.33$. HPLC: k'=2.82.

The FAB mass spectrum (537 $[M+H]^+$) confirms the assumed structure.

$^1$H NMR (250 MHz, DMSO-$d_6$): δ 12.30 (br, 1H, COOH); 9.60 (br, 1H, HC=O); 9.15 (br, 1H, Ar—OH); 8.06 (d, 1H, NH); 8.04 (d, 1H, NH); 7.98 (d, 1H, NH); 7.57 (d, 1H, NH); 6.95 (dm, 2H, ArH); 6.65 (dm, 2H, ArH); 4.55 (m, 1H, NCH); 4.48 (m, 1H, NCH); 3.90 (q, 1H, OCH); 3.00–2.40 (m, 4H, 2×$CH_2$); 2.00–1.00 (m, 3H, $CH_2$, CH); 1.12 (d, 3H, $CH_3$); 1.08 (d, 3H, $CH_3$); 0.85 (d, t, 6H, 2×$CH_3$).

The starting materials can be prepared as follows.

Compound A

O-Tetrahydropyranyl-L-lactyl-L-tyrosyl-L-valyl-L-alanine

Step A1: Methyl L-Lactate 2.7 g (30 mmol) of L-lactic acid are dissolved in 40 ml of anhydrous methanol, then 0.03 ml of concentrated sulfuric acid is added and the mixture is refluxed. At the conclusion of the reaction $[R_f(8)=0.40$ (ester), 0.08 (acid)] the solution is evaporated at a pressure of 2.0–2.5 kPa, the residue is dissolved in 20 ml of ethyl acetate, washed neutral with 15% sodium chloride solution, dried over anhydrous sodium sulfate and evaporated at a pressure of 2.0–2.5 kPa. The residue, 2.5 g (24 mmol, 80%) of an oil $[R_f(8)=0.40$, ester], is assumed to be the title product.

Step A2: O-Tetrahydropyranyl-L-lactic Acid Dicyclohexyl Ammonium Salt 0.7 g (6.7 mmol) of methyl L-lactate (Example 4, Step A1) is dissolved in 10 ml of dichloromethane, then 0.79 ml (8.6 mmol) of 3,4-dihydropyrane and 0.2 ml of HCl/EtOAc (0.11–0.15 g/ml) are added under stirring and ice cooling. Thereafter the mixture is left to stand overnight, then diluted with 10 ml of dichloromethane, washed with 2×5 ml of water, 2×5 ml of 5% NaHCO$_3$ solution and 2×5 ml of water, dried over anhydrous sodium sulfate and evaporated at a pressure of 2.0–2.5 kPa. The residual oil is methyl O-tetrahydropyranyl-L-lactate [R$_f$(8)=0.55, yield: 0.98 g (5.2 mmol), 78%)] which is dissolved in 20 ml of methanol and saponified with 1 M sodium hydroxide in the presence of thymophthalein indicator [reaction time about 4 hours, R$_f$(8)=0.45, acid]. The reaction mixture is neutralized with 1 M KHSO$_4$ and the methanol is distilled off at a pressure of 2.0–2.5 kPa. The aqueous residue is made alkaline with 1 M sodium hydroxide (1–2 ml), extracted with 5 ml of diethyl ether, acidified with 1 M KHSO$_4$ (pH=3–4), saturated with sodium chloride and extracted with 3×5 ml of ethyl acetate. The combined ethyl acetate extracts are washed with a 15% sodium chloride solution, dried over anhydrous sodium sulfate and evaporated at a pressure of 2.02.5 kPa. The residual oil is O-tetrahydropyranyl-L-lactic acid [R$_f$(8)=0.45, yield: 0.78 g (4.5 mmol, 86%)] which is dissolved in 5 ml of diethyl ether, and then 1.2 ml (6 mmol) of dicyclohexylamine are added. The solution is evaporated at a pressure of 2.0–2.5 kPa. The residue (b. p.: 30–50° C.) is rubbed with 5 ml of petroleum ether and air-dried.

Yield: 0.96 g (2.7 mmol, 52%). M. p. 94–95° C. [α]$_D$=−21.9° (c=1, methanol). Analysis for C$_{20}$H$_{37}$NO$_4$ (355.504) Calculated: C %=67.56; H %=10.49; N %=3.94. Found: C %=67.6; H %=10.6; N %=3.9.

Step A3: O-Tetrahydropyranyl-L-lactic Acid 2,4,5-trichlorophenyl Ester 1.47 g (4.14 mmol) of O-tetrahydropyranyl-L-lactic acid dicyclohexyl ammonium salt (Example 4, Step A2) are dissolved in 15 ml of ethyl acetate and 5 ml of 1 M KHSO$_4$. The phases are separated, the ethyl acetate phase is washed neutral with a 15% sodium chloride solution, dried over anhydrous sodium sulfate and evaporated at a pressure of 2.0–2.5 kPa. The residual oil—O-tetrahydropyranyl-L-lactic acid (0.64 g, 3.67 mmol)—is dissolved in 5 ml of tetrahydrofuran and cooled to 0° C. Under constant stirring 0.79 g (4 mmol) of 2,4,5-trichlorophenol and 0.79 g (3.85 mmol) of dicyclohexylcarbodiimide are added. The reaction mixture is left to stand for 5 hours. The separated dicyclohexylurea is filtered off and the filtrate is evaporated at a pressure of 2.0–2.5 kPa. The residue is 1.47 g (4 mmol) of the product [R$_f$(8)=0.72] containing 1–2% of 2,4,5-trichlorophenol [R$_f$(8)=0.62] and dicyclohexylurea [R$_f$(B)=0.55].

Step A4: Methyl O-tetrahydropyranyl-L-lactyl-L-tyrosyl-L-valyl-L-alaninate 0.72 9 (2 mmol) of O-tetrahydropyranyl-L-lactic acid 2,4,5-trichlorophenyl ester (Example 4, Step A3) and 0.55 g (1.5 mmol) of methyl L-tyrosyl-L-valyl-L-alaninate (Example 1, Step A3) are dissolved in 5 ml of dimethylformamide. The reaction mixture is left to stand overnight, then it is evaporated at a pressure of 2.0–2.5 kPa. The residue is dissolved in 5 ml of ethyl acetate and 5 ml of 1 M KHSO$_4$, the ethyl acetate layer is washed neutral with water, dried over anhydrous sodium sulfate and evaporated at 2.0–2.5 kPa. The residue is rubbed with ether, filtered, washed with diethyl ether and dried in a vacuum desiccator.

Yield: 0.58 g (1.11 mmol, 74%). R$_f$(1)=0.60.

Step A5: O-Tetrahydropyranyl-L-lactyl-L-tyrosyl-L-valyl-L-alanine 0.525 g (1 mmol) of methyl O-tetrahydropyranyl-L-lactyl-L-tyrosyl-L-valyl-L-alaninate (Example 4, Step A4) is dissolved in 5 ml of acetone and saponified with 1 M sodium hydroxide in the presence of thymolphthalein indicator. The reaction time amounts to about 3 hours. Thereafter the reaction mixture is neutralized with 1 M KHSO$_4$ and the acetone is distilled off at a pressure of 2.0–2.5 kPa. After adding 5 ml of water the pH of the residue is adjusted with 1 M sodium hydroxide to a valu of 8–9, extracted with 5 ml of diethyl ether and acidified with 1 M KHSO$_4$ to about pH=3. The separated oil is extracted with 3×5 ml of ethyl acetate, the combined ethyl acetate solutions are washed neutral with water, dried over anhydrous sodium sulfate and evaporated at a pressure of 2.0–2.5 kPa. The residue is rubbed with diethyl ether, filtered, washed with diethyl ether and dried in a vacuum desiccator.

Yield: 0.34 g (0.67 mmol, 67%). R$_f$(4)=0.30. [α]$_D$=−51.8° (c=0.5, methanol).

The FAB mass spectrum (508 [M+H]$^+$) confirms the assumed structure.

EXAMPLE 5

(3R)-3-(L-Lactyl-L-tyrosyl-L-isoleucyl-L-alanylamino)-4-carboxy-butyraldehyde

Step 1: (3R)-3-(L-Lactyl-L-tyrosyl-L-isoleucyl-L-alanyl-amino)-4-t-butoxycarbonyl-butyraldehyde Diethyl Acetal Starting from 0.26 g (0.5 mmol) of O-tetrahydropyranyl-L-lactyl-L-tyrosyl-L-isoleucyl-L-alanine (Example 5, Step A4) and 0.13 g (0.5 mmol) of (3R)-3-amino-4-t-butoxycarbonyl-butyraldehyde diethyl acetal (Example 1, Step B4), applying the procedure described in Example 4, Step 1 and using proportional amounts of reagents and solvents, the components are coupled and the end product is isolated.

Yield: 0.11 g (0.14 mmol, 30%). R$_f$(1)=0.55.

The FAB mass spectrum (765 [M+H]$^+$) confirms the assumed structure.

Step 2: (3R)-3-(L-Lactyl-L-tyrosyl-L-isoleucyl-L-alanyl-amino)-4-carboxybutyraldehyde 0.10 g (0.13 mmol) of the protected peptide-aldehyde (Example 5, Step 1) is transformed by the method applied in Example 4, Step 2.

Yield: 0.03 g (0.05 mmol, 42%) R$_f$(4)=0.35. HPLC: k'=3.52.

The FAB mass spectrum (551 [M+H]$^+$) confirms the assumed structure.

$^1$H NMR (250 MHz, DMSO-d$_6$); δ 12.30 (br, 1H, COOH); 9.60 (t, 1H, HC=O); 9.14 (s, 1H, ArOH); 8.12 (d, 2H, 2×NH); 8.02 (d, 1H, NH); 7.57 (d, 1H, NH); 6.90 (dm, 2H, ArH); 6.59 (dm, 2H, ArH); 5.40 (br, 1H, OH); 4.52 (m, 1H, NCH); 4.43 (m, 1H, NCH); 4.10 (m, 2H, 2×NCH); 3.90 (q, 1H, OCH); 3.00–2.40 (m, 4H, 2×CH$_2$); 1.80–1.00 (m, 5H, 2×CH$_2$, CH); 1.17 (d, 3H, CH$_3$); 1.08 (d, 3H, CH$_3$); 0.85 (d, 3H, CH$_3$); 0.82 (t, 3H, CH$_3$).

The starting materials can be prepared as follows.

Compound A

O-Tetrahydropyranyl-L-lactyl-L-tyrosyl-L-isoleucyl-L-alanine

Step A1: Methyl Benzyloxycarbonyl-L-tyrosyl-L-isoleucyl-L-alaninate 3.06 g (10 mmol) of methyl L-isoleucyl-L-alaninate hydrogen oxalate (Example 3, Step A4) and 4.94 g (10 mmol) of benzyloxycarbonyl-L-tyrosine 2,4,5-trichlorophenyl ester are condensed according to the method described in Example 1, Step A2, using proportional amounts of reagents and solvents.

Yield: 3.75 g (7.3 mmol, 73%). R$_f$(5)=0.80. M. p.: 167–169° C. [α]$_D$=−36.8° (c=1, methanol). Analysis for C$_{27}$H$_{35}$N$_3$O$_7$ (513.354) Calculated: C %=63.14; H %=6.87; N %=8.18. Found: C %=62.0; H %=6.8; N %=8.15

Step A2: Methyl L-Tyrosyl-L-isoleucyl-L-alanylate 3.6 g (7 mmol) of methyl benzyloxycarbonyl-L-tyrosyl-L-isoleucyl-L-alaninate (Example 5, Step A1) are dissolved in 70 ml of dimethylformamide and hydrogenated in the presence of 0.15 g of Pd/C catalyst. At the conclusion of the reaction [$R_f(6)=0.20$] the catalyst is filtered off and the filtrate is evaporated at a pressure of 2.0–2.6 kPa. The residue is rubbed with diethyl ether, the precipitate is filtered, washed with diethyl ether and dried in a vacuum desiccator.

Yield: 2.33 g (6.16 mmol, 88%). $R_f(7)$ 0.50.

Step A3: Methyl O-tetrahydropyranyl-L-lactyl-L-tyrosyl-L-iso-leucyl-L-alaninate 0.57 g (1.5 mmol) of methyl L-tyrosyl-L-isoleucyl-L-alaninate (Example 5, Step A2) and 0.54 g (1.5 mmol) of O-tetrahydropyranyl-L-lactic acid 2,4,5-trichlorophenyl ester (Example 4, Step A3) are dissolved in 5 ml of dimethylformamide. The solution is left to stand for 4 hours, then evaporated at 2.0–2.5 kPa. The residue is dissolved in 10 ml of ethyl acetate, washed with 3×5 ml of 1 M KHSO$_4$ and 3×5 ml of water, dried over anhydrous sodium sulfate and evaporated at a pressure of 2.0–2.5 kPa. The residue is an oil (0.8 g) [$R_f(1)=0.55$] which is directly used in the next step.

Step A4: O-Tetrahydropyranyl-L-lactyl-L-tyrosyl-L-isoleucyl-L-alanine 0.8 g (1.5 mmol) of methyl O-tetrahydropyranyl-L-lactyl-L-tyrosyl-L-isoleucyl-L-alanylate (Example 5, Step A3) is saponified according to the method applied in Example 4, Step A5, using proportional amounts of reagents and solvents.

Yield: 0.37 g (0.71 mmol, 47%). $R_f(4)=0.70$. [α]$_D$=−56.05° (c=0.5, methanol).

The FAB mass spectrum (552 [M+H]$^+$) confirms the assumed structure.

EXAMPLE 6

(3R)-3-L-Phenyllactyl-L-valyl-L-alanylamino)-4-carboxy-butyraldehyde

Step 1: (3R)-3-(L-Phenyllactyl-L-valyl-L-alanylamino)-4-t-butoxycarbonyl-butyraldehyde Diethyl Acetal 0.21 g (0.5 mmol) of O-tetrahydropyranyl-L-phenyllactyl-L-valyl-L-alanine (Example 6, Step A5) and 0.13 g (0.5 mmol) of (3R)-3-amino-4-t-butoxycarbonyl-butyraldehyde diethyl acetal (Example 1, Step B4) are coupled according to the method described in Example 1, Step 1, using proportional amounts of reagents and solvents, then the end product is isolated.

Yield: 0.17 g (0.25 mmol, 50%). $R_f(1)=0.65$.

The FAB mass spectrum (664 [M+H]$^+$) confirms the assumed structure.

Step 2: (3R)-3-(L-Phenyllactyl-L-valyl-L-alanylamino)-4-carboxybutyraldehyde 0.1 g (0.15 mmol) of the protected peptide-aldehyde (Example 6, Step 1) is dissolved in 2 ml of trifluoroacetic acid and left to stand at room temperature for 2 hours, then the mixture is diluted with 10 ml of diisopropyl ether and left to stand in the refrigerator for 3 hours. The formed precipitate is filtered, washed with diisopropyl ether and dried in a vacuum desiccator.

Yield: 0.03 g (0.06 mmol) $R_f(5)=0.40$. HPLC: k'=4.46.

The FAB mass spectrum (450 [M+H]$^+$) confirms the assumed structure.

$^1$H NMR (250 MHz, DMSO-d$_6$): δ 12.30 (br, 1H, COOH); 9.50 (br, 1H, HC=O); 8.25 (d, 1H, NH); 8.16 (d, 1H, NH); 7.52 (d, 1H, NH); 7.20 (m, 5H, ArH); 4.38 (m, 1H, HCO); 4.20–4.05 (m, 3H, 3×NCH); 3.00 (dd, 1H, CH); 2.75 (dd, 1H, CH); 2.40 (d, 2H, CH$_2$); 1.90 (m, 1H, CH); 2.00–1.00 (m, 2H, CH$_2$); 1.12 (d, 3H, CH$_3$); 0.75 (d, 3H, CH$_3$); 0.70 (d, 3H, CH$_3$).

The starting materials can be prepared as follows.

Compound A

O-Tetrahydropyranyl-L-phenyllactyl-L-valyl-L-alanine

Step A1: Methyl L-Phenyllactate 3.32 g (20 mmol) of L-phenyllactic acid are dissolved in 40 ml of anhydrous methanol, 0.02 ml of concentrated sulfuric acid is added and the mixture is refluxed. At the conclusion of the reaction [$R_f(8)=0.55$ (ester), 0.10 (acid)] the mixture is evaporated at a pressure of 2.0–2.5 kPa, the residue is dissolved in 20 ml of ethyl acetate, washed neutral with water, dried over anhydrous sodium sulfate and evaporated at a pressure of 2.0–2.5 kPa. The residue is an oil (3.02 g, 16.7 mmol, 83%) [$R_f(8)=0.55$] assumed to be the title product.

Step A2: O-Tetrahydropyranyl-phenyllactic Acid Dicyclohexyl Ammonium Salt 3.0 g (16.65 mmol) of methyl L-phenyllactate (Example 6, Step A1) are dissolved in 30 ml of dichloromethane. Under stirring and ice-cooling 2.0 g (21.8 mmol) of 3,4-dihydropyran and 0.5 ml of HCl/EtOAc (0.11–0.15 g/ml) are added and the solution is left to stand overnight. Then the reaction mixture is diluted with 25 ml of dichloromethane, washed with 2×10 ml of water, 2×10 ml of 5% NaHCO$_3$ solution and 2×10 ml of water, dried over anhydrous sodium sulfate and evaporated at a pressure of 2.0–2.5 kPa. The residual oil is methyl O-tetrahydropyranyl-L-phenyllactate [$R_f(8)=0.60$, yield: 3.8 g (14.4 mmol, 86%)] which is dissolved in 50 ml of methanol and saponified with 1 M sodium hydroxide in the presence of thymolphthalein indicator [the reaction time amounts to about 4 hours $R_f(8)=0.45$ (acid)]. The reaction mixture is neutralized with 1 M KHSO$_4$ and the methanol is distilled off at a pressure of 2.0–2.5 kPa. The residual aqueous solution is made alkaline with 1 M sodium hydroxide (1–2 ml), extracted with 5 ml of diethyl ether, acidified with 1 M KHSO$_4$ (pH=3–4) and extracted with 3×10 ml of ethyl acetate. The combined ethyl acetate extracts are washed with water, dried over anhydrous sodium sulfate and evaporated at a pressure of 2.0–2.5 kPa. The residual oil is O-tetrahydropyranyl-L-phenyllactic acid [$R_f(8)$ 0.45, yield: 3.92 g (9.09 mmol, 63%)] which is dissolved in 15 ml of diethyl ether, then 1.8 ml (9 mmol) of dicyclohexylamine are added and the solution is left to stand in the refrigerator overnight. The precipitated product is filtered. washed with diethyl ether and air-dried.

Yield: 3.45 g (8 mmol, 57%). M. p.: 147° C. [α]$_D$=−8.96° (c=1, methanol). Analysis for C$_{26}$H$_{41}$ NO$_4$ (431.596) Calculated: C %=72.35; H %=9.58; N %=3.24. Found: C %=72.5; H %=9.65; N %=3.0

Step A3: O-Tetrahydropyranyl-phenyllactic Acid 2,4,5-trichlorophenyl Ester 1.7 g (4 mmol) of O-tetrahydropyranyl-phenyllactic acid dicyclohexylammonium salt (Example 6, Step A2) are dissolved in 15 ml of ethyl acetate and 5 ml of 1 M KHSO$_4$. The phases are separated, the ethyl acetate phase is washed neutral with a 15% sodium chloride solution, dried over anhydrous sodium sulfate and evaporated at a pressure of 2.0–2.5 kPa. The oily residue is dissolved in 5 ml of tetrahydrofuran and cooled to 0° C. Under constant stimng 0.87 g (4.4 mmol) of 2,4,5-trichlorophenol and 0.86 g (4.2 mmol) of dicyclohexylcarbodiimide are added, then the reaction mixture is left to stand for about 5 hours. The precipitated dicyclohexyurea is filtered off and the filtrate is evaporated at a pressure of 2.0–2.5 kPa. The residue is rubbed with n-hexane, filtered, washed with n-hexane and air-dried.

Yield: 0.92 g (2.14 mmol). $R_f(8)$=0.73. M. p.: 110–116° C. Analysis for $C_{20}H_{19}O_4Cl_3$ (429.723) Calculated: C %=55.90; H %=4.46; N %=24.75. Found: C %=56.7; H %=4.8; N %=24.1.

Step A4: Methyl O-Tetrahydropyranyl-L-phenyllactyl-L-valyl-L-alaninate

Starting from 0.55 g (1.9 mmol) of methyl L-valyl-L-alaninate hydrogen oxalate (Example 1, Step A1) and 0.82 g (1.9 mmol) of O-tetrahydropyranyl-phenyllactic acid 2,4,5-trichlorophenyl ester (Example 6, Step A3) and using proportional amounts of reagents and solvents, the procedure described in Example 4, Step A4 is applied for the condensation of the components and the isolation of the product, except, that the evaporation residue is rubbed with petroleum ether.

Yield: 0.6 g (1.43 mmol, 75%). $R_f(1)$=0.55. M. p.: 124–125° C. $[\alpha]_D$=−39.8° (c=1, methanol). Analysis for $C_{23}H_{34}N_2O_6$ (434.518) Calculated: C %=63.57; H %=7.89; N %=6.45. Found: C %=64.0; H %=8.15; N %=6.5.

Step A5: O-Tetrahydropyranyl-L-phenyllactyl-L-valyl-L-alanine 0.46 g (1.1 mmol) of methyl O-tetrahydropyranyl-L-phenyllactyl-L-valyl-L-alaninate (Example 6, Step A4) is dissolved in 5 ml of acetone and saponified with 1 M sodium hydroxide in the presence of thymolphthalein indicator. The reaction time is about 3 hours. Then the reaction mixture is neutralized with 1 M $KHSO_4$ and the acetone is distilled off at a pressure of 2.0–2.5 kPa. 5 ml of water are added to the residue and the pH is adjusted to 8–9 with 1 M sodium hydroxide, then the solution is extracted with 5 ml of diethyl ether and acidified to pH 3 with 1 M $KHSO_4$. The separated oil is extracted with 3×5 ml of ethyl acetate. The combined ethyl acetate extracts are washed neutral with water, dried over anhydrous sodium sulfate and evaporated at a pressure of 2.0–2.5 kPa.

Yield: 0.4 g (1 mmol, 91%) of solidified foam. $R_f(1)$= 0.30.

The FAB mass spectrum (421 $[M+H]^+$) confirms the assumed structure.

Analysis for $C_{22}H_{32}N_2O_6 \cdot \frac{1}{2}H_2O$ (429.519) Calculated: C %=61.59; H %=7.73; N %=6.53. Found: C %=61.3; H %=7.75; N %=6.25.

EXAMPLE 7

(3R)-3-(Acetyl-L-tyrosyl-L-isoleucyl-L-alanylamino)-4-carboxybutyraldehyde

Step 1: (3R)-3-(Acetyl-L-tyrosyl-L-isoleucyl-L-alanyl-amino)-4-t-butoxycarbonyl-butyraldehyde Diethyl Acetal 0.24 g (0.6 mmol) of acetyl-L-tyrosyl-L-isoleucyl-L-alanine (Example 7, Step A2) and 0.16 g (0.6 mmol) of (3R)-3-amino-4-t-butoxycarbonyl-butyraldehyde diethyl acetal (Example 1, Step B4) are coupled and the end product is isolated according to the method described in Example 1, Step 1, using proportional amounts of reagents and solvents.

Yield: 0.36 g (0.58 mmol, 96%). $R_f(5)$ 0.75.

The FAB mass spectrum (651 $[M+H]^+$) confirms the assumed structure.

Step 2: (3R)-3-(Acetyl-L-tyrosyl-L-isoleucyl-L-alanylamino)-4-carboxybutyraldehyde 0.19 g (0.3 mmol) of the protected peptide-aldehyde (Example 7, Step 1) is transformed according to the method applied in Example 1, Step 2, using proportional amounts of reagents and solvents.

Yield: 0.15 g (95%). $R_f(5)$=0.30. HPLC: k'=3.4.

The FAB and ESI mass spectra (521$[M+H]^+$) confirm the assumed structure.

$^1$H NMR (250 MHz, DMSO-$d_6$): δ 12.30 (br, 1H, COOH); 9.57 (br, 1H, HC=O); 7.99 (d, 1H, NH); 7.98 (d, 1H, NH); 7.96 (d, 1H, NH); 7.87 (d, 1H, NH); 7.02 (dm, 2H, ArH); 6.62 (dm, 2H, ArH); 4.45 (m, 2H, 2×NCH); 4.21 (m, 2H, 2×NCH); 3.00–2.40 (m, 4H, 2×$CH_2$); 1.74 (s, 3H, $CH_3CO$); 2.00–1.00 (m, 3H, CH, $CH_2$); 1.15 (d, 3H, $CH_3$); 0.85 (d, t, 6H, 2×$CH_3$).

The starting materials can be prepared as follows.

Compound A

Acetyl-L-tyrosyl-L-isoleucyl-L-alanine

Step A1: Methyl Acetyl-L-tyrosl-L-isoleucyl-L-alaninate 1.9 g (5 mmol) of methyl L-tyrosyl-L-isoloucyl-L-alaninate (Example 5, Step A2) are dissolved in 15 ml of anhydrous pyridine, cooled to 0° C., then under constant stirring 1.0 ml of acetic anhydride is introduced. The reaction mixture is stirred without cooling for 2 hours, then it is evaporated at 2.0–2.5 kPa. The residue is dissolved in 25 ml of ethyl acetate, washed neutral with water, dried over anhydrous sodium sulfate and evaporated at a pressure of 2.0–2.5 kPa. The solid residue is rubbed with diethyl ether, filtered, washed with diethyl ether and dried in a vacuum desiccator.

Yield: 1.5 g (3.56 mmol, 71%). $R_f(6)$=0.60. $[\alpha]_D$=−39.3° (c=1, methanol). Analysis for $C_{21}H_{31}N_3O_6 \cdot \frac{1}{2}H_2O$ (430.490) Calculated: C %=58.59; H %=7.49; N %=9.76. Found: C %=58.0; H %=7.3; N %=9.4.

Step A2: Acetyl-L-tyrosyl-L-isoleucyl-L-alanine 1.0 g (2.37 mmol) of methyl acetyl-Lrlyrosyl-L-isoleucyl-L-alaninate (Example 7, Step A1) is dissolved in 10 ml of methanol and saponified with 1 M sodium hydroxide in the presence of thymolphthalein indicator. The reaction mixture is concentrated to 3–5 ml at a pressure of 2.0–2.5 kPa, the concentrate is diluted with 10 ml of water, acidified with 1 M $KHSO_4$ to pH 3, extracted with 3×10 ml of n-butanol saturated with water, the combined n-butanol solutions are washed with 3×10 ml of water saturated with n-butanol and evaporated at a pressure of 2.0–2.5 kPa The residue is crystallized with diethyl ether, filtered, washed with diethyl ether and dried in a vacuum desiccator.

Yield: 0.70 g (1.72 mmol, 73%). $R_f(7)$=0.55. $[\alpha]_D$=−24.5° (c 1, methanol).

The FAE mass spectrum (408 $[M+H]^+$) confirms the assumed structure.

Analysis for $C_{20}H_{29}N_3O_6 \cdot \frac{1}{2}H_2O$ (416.464) Calculated: C %=57.67; H %=7.26; N %=10.09. Found: C %=57.65; H %=7.3; N %=9.5.

We claim:

1. (3R)-3-Amino-4-carboxybutyraldehyde derivatives of general formula (I),

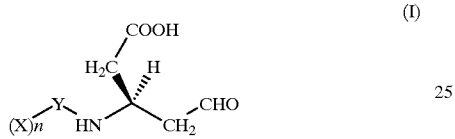

wherein
- X represents a $C_{1-4}$ alkyloxycarbonyl, an optionally substituted phenyl-($C_{1-2}$ alkyloxy)carbonyl, a $C_{1-4}$ alkylcarbonyl or an optionally substituted phenyl-($C_{1-3}$ alkyl)carbonyl group,
- n represents 1 or 0,
- Y represents, in the case when n=1, a tetrapeptide of general formula $Y_4$-$Y_3$-$Y_2$-$Y_1$, a tripeptide of general formula $Y_3$-$Y_2$-$Y_1$ or a dipeptide of general formula $Y_2$-$Y_1$ or an amino acid residue of general formula $Y_1$, or in the case when n=0, an α-hydroxyacyl-tripeptide of general formula $Q_4$-$Y_3$-$Y_2$-$Y_1$, an α-hydroxyacyl-dipeptide of general formula $Q_3$-$Y_2$-$Y_1$ or an α-hydroxyacyl-aminoacyl residue of general formula $Q_2$-$Y_1$,
- wherein $Y_1$-$Y_4$ represent a residue selected from the group consisting of the following L- or D-amino acids: alanine, alloisoleucine, cyclohexyl-glycine, phenylalanine, glutamine, histidine, isoleucine, leucine, lysine, methionine, pipecolic acid, proline, tyrosine and valine; and $Q_2$–$Q_4$ represent an acyl group selected from the group consisting of the following α-hydroxyacids of R or S configuration: 2-cycloheptyl-2-hydroxy-acetic acid, 2-cyclohexyl-2-hydroxyacetic acid, 3-cyclohexyllactic acid, 3-phenyllactic acid, 2-hydroxy-3-methylbutyric acid, 2-hydroxy-3-methylvaleric acid, mandelic acid or lactic acid, and salts thereof formed with organic or inorganic bases.

2. A pharmaceutical composition which comprises as active ingredient at least one compound of general formula (I), wherein the meanings of X, n and Y are as defined in claim 1, or a pharmaceutically acceptable salt thereof in admixture with carriers and additives.

3. Compounds of general formula (I), wherein the meanings of X, n and Y are as defined in claim 1, or a pharmaceutically acceptable salt thereof for use as a medicine.

4. (3R)-3-(Acetyl-L-tyrosyl-L-valyl-L-alanylamino)-4-carboxybutyraldehyde and salts thereof formed with organic or inorganic bases.

5. (3R)-3-(Ethoxycarbonyl-L-alanyl-L-tyrosyl-L-valyl-L-alanylamino)-4-carboxybutyraldehyde and salts thereof formed with organic or inorganic bases (SEQ ID NO:1).

6. (3R)-3-[(2S)-(2-hydroxypropionyl)-L-tyrosyl-L-valyl-L-alanylamino]-4-carboxybutyraldehyde and salts thereof formed with organic or inorganic bases.

* * * * *